US011491000B2

(12) United States Patent
Cardinale et al.

(10) Patent No.: US 11,491,000 B2
(45) Date of Patent: Nov. 8, 2022

(54) APPLICATOR INSTRUMENTS HAVING STACKED SURGICAL FASTENERS FOR OFF-AXIS SURGICAL FASTENER DELIVERY

(71) Applicant: Ethicon, Inc., Somerville, NJ (US)

(72) Inventors: Michael Cardinale, Morristown, NJ (US); Doug Souls, Andover, NJ (US); Anthony Miksza, Nazareth, PA (US); Aaron J. Brickner, Fostoria, OH (US); Jared Schneider, Cranston, RI (US); Todd Sack, Philadelphia, PA (US); David R. Schiff, Highland Park, NJ (US); Erin Elizabeth Wenig, High Point, NC (US)

(73) Assignee: Ethicon, Inc., Raritan, NJ (US)

( * ) Notice: Subject to any disclaimer, the term of this patent is extended or adjusted under 35 U.S.C. 154(b) by 767 days.

(21) Appl. No.: 16/421,805

(22) Filed: May 24, 2019

(65) Prior Publication Data

US 2019/0274806 A1  Sep. 12, 2019

Related U.S. Application Data

(63) Continuation of application No. 14/979,909, filed on Dec. 28, 2015, now Pat. No. 10,299,905.

(51) Int. Cl.
*A61F 2/00* (2006.01)
*A61B 17/068* (2006.01)
(Continued)

(52) U.S. Cl.
CPC ........ *A61F 2/0063* (2013.01); *A61B 17/0682* (2013.01); *A61B 17/064* (2013.01);
(Continued)

(58) Field of Classification Search
CPC ........... A61F 2/0063; A61F 2002/0072; A61B 17/0682; A61B 17/064
See application file for complete search history.

(56) References Cited

U.S. PATENT DOCUMENTS 3,664,408 A   5/1972 Eibe
3,740,994 A   6/1973 Decarlo, Jr.
(Continued)

FOREIGN PATENT DOCUMENTS

CN   103006283   4/2013
CN   103338712   10/2013
(Continued)

OTHER PUBLICATIONS

International Search Report issued in corresponding International Application No. PCT/US2016/066922, dated May 18, 2017, 4 pages.

*Primary Examiner* — Ashley L Fishback

(57) ABSTRACT

An applicator instrument for dispensing surgical fasteners includes a housing, and an elongated shaft extending from the housing. The elongated shaft has a proximal end secured to the housing, a distal end spaced from the proximal end, and a first axis extending between the proximal and distal ends of the elongated shaft. Surgical fasteners are disposed in the elongated shaft. The surgical fasteners are stacked at an angle relative to the first axis of the elongated shaft. A distal end cap having a surgical fastener dispensing window is secured to the distal end of the elongated shaft. The applicator instrument has a firing system disposed in the housing, and an actuator coupled with the firing system for activating the firing system to dispense the surgical fasteners through the surgical fastener dispensing window.

19 Claims, 30 Drawing Sheets

(51) Int. Cl.
*A61B 17/064* (2006.01)
*A61B 17/29* (2006.01)
*A61B 90/00* (2016.01)
*A61B 17/00* (2006.01)

(52) U.S. Cl.
CPC ........... *A61B 2017/0042* (2013.01); *A61B 2017/00738* (2013.01); *A61B 2017/2904* (2013.01); *A61B 2017/2908* (2013.01); *A61B 2017/2923* (2013.01); *A61B 2017/2943* (2013.01); *A61B 2090/0807* (2016.02); *A61F 2002/0072* (2013.01)

(56) References Cited

U.S. PATENT DOCUMENTS

| | | |
|---|---|---|
| 4,471,780 A | 9/1984 | Menges et al. |
| 4,478,220 A | 10/1984 | DiGiovanni et al. |
| 4,612,933 A | 9/1986 | Brinkerhoff et al. |
| 5,203,864 A | 4/1993 | Phillips |
| 5,290,297 A | 3/1994 | Phillips |
| 5,413,272 A | 5/1995 | Green et al. |
| 5,470,010 A | 11/1995 | Rothfuss et al. |
| 5,582,616 A | 12/1996 | Bolduc et al. |
| 5,601,573 A | 2/1997 | Berg et al. |
| 5,810,882 A | 9/1998 | Bolduc et al. |
| 5,830,221 A | 11/1998 | Stein et al. |
| 5,833,700 A | 11/1998 | Fogelberg et al. |
| 5,921,997 A | 7/1999 | Fogelberg et al. |
| 7,485,124 B2 | 2/2009 | Kuhns et al. |
| 7,887,553 B2 | 2/2011 | Lehman et al. |
| 8,216,272 B2 | 7/2012 | Shipp |
| 8,282,670 B2 | 10/2012 | Shipp |
| 8,474,679 B2 | 7/2013 | Felix |
| 8,579,920 B2 | 11/2013 | Nering et al. |
| 8,728,098 B2 | 5/2014 | David et al. |
| 8,728,099 B2 | 5/2014 | Cohn et al. |
| 8,870,049 B2 * | 10/2014 | Amid ............... A61B 17/0684 227/176.1 |
| 8,894,669 B2 | 11/2014 | Nering et al. |
| 8,920,439 B2 | 12/2014 | Cardinale et al. |
| 9,364,228 B2 | 6/2016 | Straehnz et al. |
| 10,299,905 B2 | 5/2019 | Cardinale et al. |
| 2005/0085830 A1 | 4/2005 | Lehman et al. |
| 2010/0204717 A1 | 8/2010 | Knodel |
| 2010/0312258 A1 | 12/2010 | Shipp |
| 2010/0327042 A1 | 12/2010 | Amid et al. |
| 2011/0079627 A1 | 4/2011 | Cardinale et al. |
| 2013/0303845 A1 | 11/2013 | Skula et al. |
| 2013/0304091 A1 | 11/2013 | Straehnz et al. |
| 2013/0304092 A1 | 11/2013 | Cardinale et al. |

FOREIGN PATENT DOCUMENTS

| | | |
|---|---|---|
| CN | 103417211 | 12/2013 |
| JP | 2011515125 | 5/2011 |
| JP | 2015517348 | 6/2015 |

\* cited by examiner

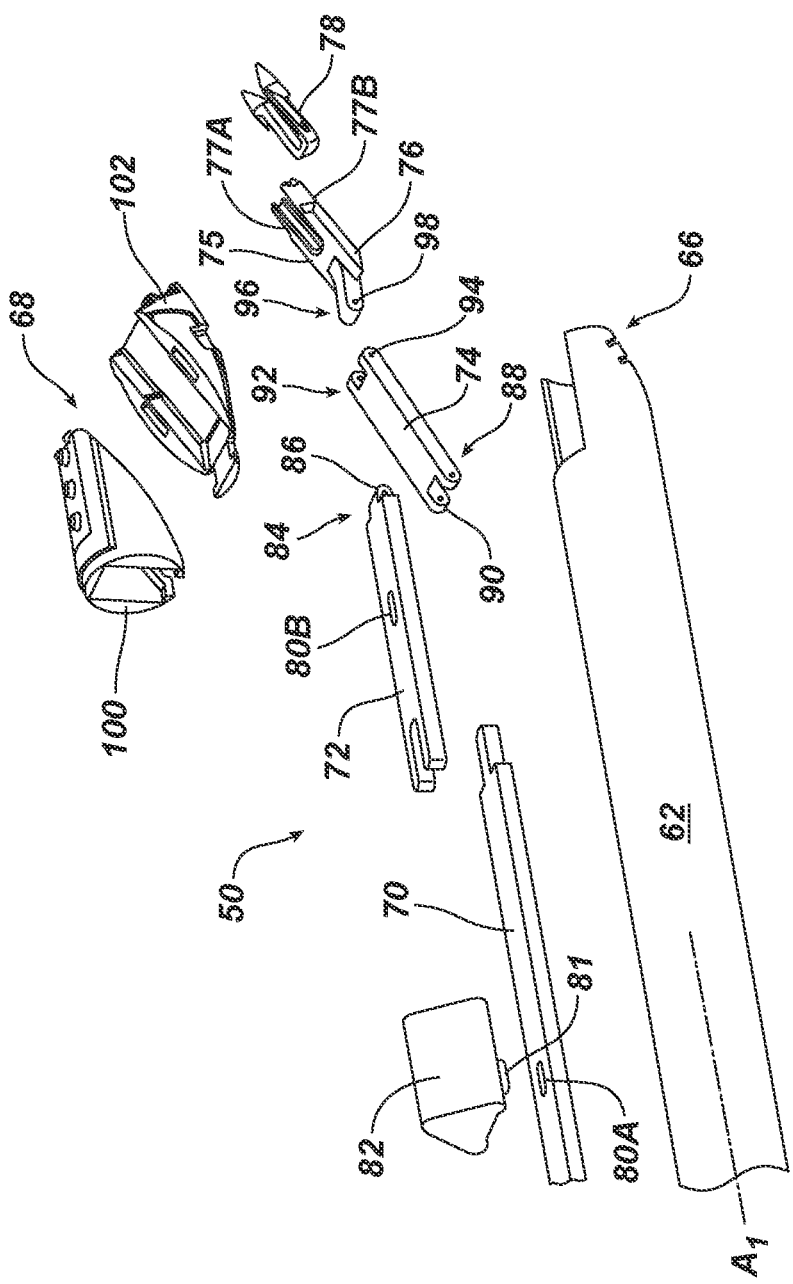

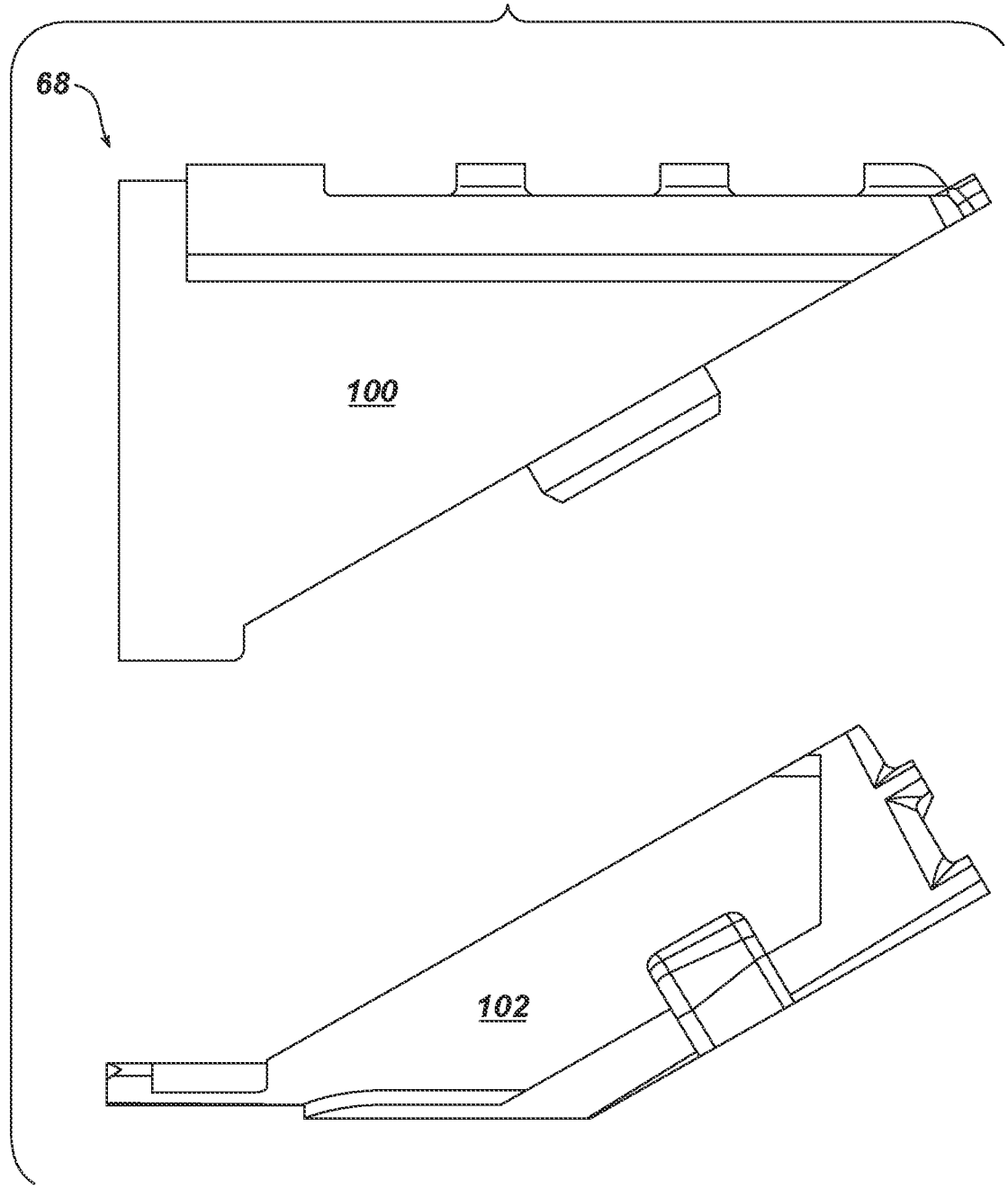

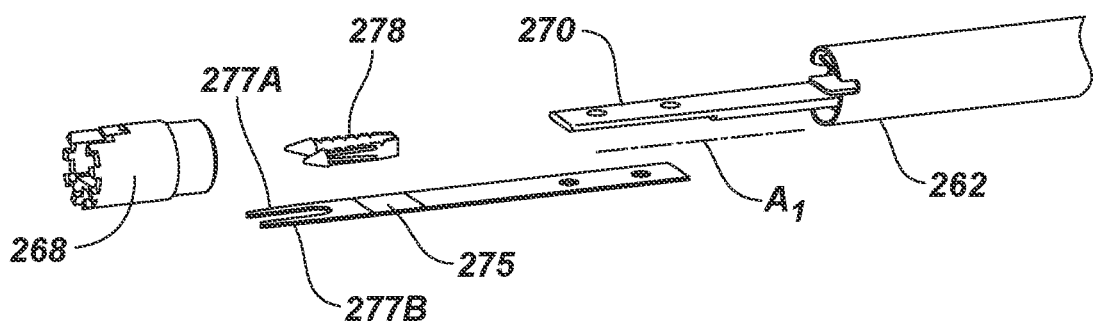
FIG. 16
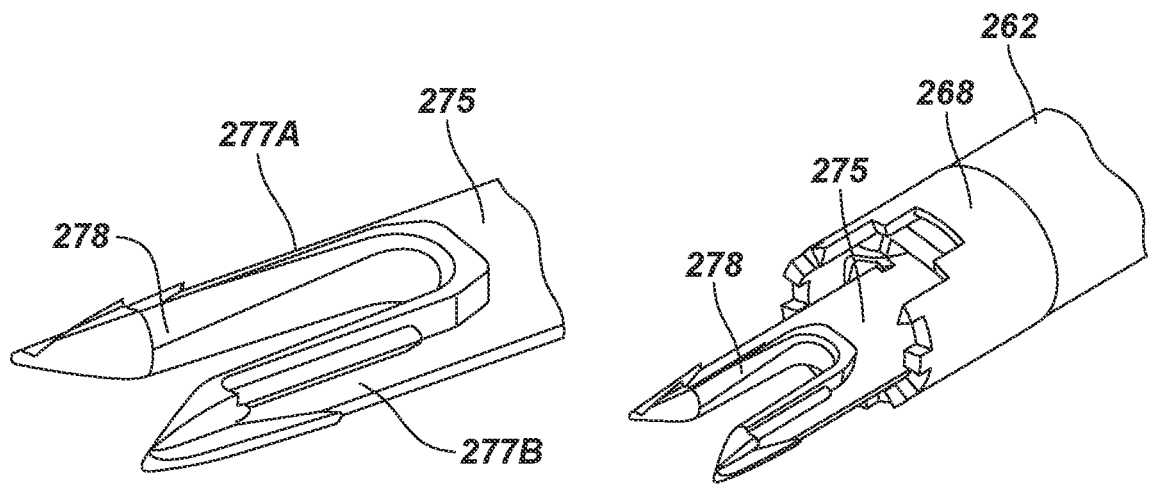
FIG. 17A
FIG. 17B
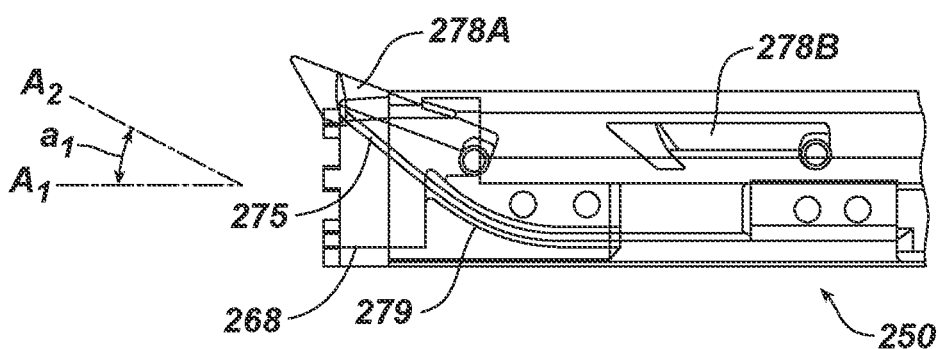
FIG. 18

APPLICATOR INSTRUMENTS HAVING STACKED SURGICAL FASTENERS FOR OFF-AXIS SURGICAL FASTENER DELIVERY

CROSS-REFERENCE TO RELATED APPLICATIONS

The present patent application is a continuation of U.S. patent application Ser. No. 14/979,909, filed Dec. 28, 2015, now allowed, the disclosure of which is hereby incorporated by reference herein.

BACKGROUND OF THE INVENTION

Field of the Invention

The present application is generally related to medical devices used for surgical procedures, and is more specifically related to applicator instruments, systems and methods for deploying surgical fasteners for securing prosthetic devices.

Description of the Related Art

A hernia is a condition where a small loop of bowel or intestine protrudes through a weak place or defect within the abdominal muscle wall or groin of a patient. This condition commonly occurs in humans, particularly males. Hernias may result from a congenital defect whereby the patient is born predisposed with this condition, prior abdominal surgery, or may be caused by straining or lifting heavy objects. Heavy lifting may be known to create a large amount of stress upon the abdominal wall and can cause a rupture or tearing at a weak point of the abdominal muscle to create the defect or opening. In any case, the patient may be left with an unsightly bulge of intestinal tissue protruding through the defect, which may result in pain, reduced lifting abilities, and in some cases, impaction of the bowel, or possibly other complications if the flow of blood is cut off to the protruding tissue.

A common solution to the above-described problem may be surgery. During a surgical procedure, the defect is accessed and carefully examined, either through an open incision or endoscopically through an access port such as a trocar. In either case, careful examination is required due to the network of vessels and nerves which exist in the area of a typical defect, which requires a surgeon to conduct a hernia repair with great skill and caution. Within this area can be found vascular structures such as gastric vessels, the external iliac vessels, and the inferior epigastric vessels, as well as reproductive vessels such as the vas deferens extending through the inguinal floor.

Once the surgeon is familiar with the anatomy of a patient, the surgeon carefully places the viscera back into the patient's abdomen through the defect. Repairing the defect can involve closure of the defect with sutures or fasteners but generally involves placing a surgical prosthetic such as a mesh patch over the defect, and attaching the mesh patch to the abdominal wall or inguinal floor with conventional suture or with surgical fasteners. The mesh patch acts as a barrier and prevents expulsion of bowel through the defect. Suturing of the mesh patch to the inguinal floor can be well suited to open procedures but can be much more difficult and time consuming with endoscopic procedures. With the adoption of endoscopic surgery, endoscopic surgical instruments that apply surgical fasteners can be used. However, the tissue of the inguinal floor may offer special challenges to the surgeon when a needle or fastener is used to penetrate structures such as Cooper's ligament.

At present, there are a variety of surgical instruments and fasteners available for the surgeon to use in an endoscopic or open procedure to attach the mesh patch to the inguinal floor. One of the earliest types of endoscopic surgical instruments used is a surgical stapler. A plurality or stack of these unformed staples may be generally contained within a stapling cartridge in a serial fashion, and may be sequentially advanced or fed within the instrument by a spring mechanism. A secondary valving or feeding mechanism may be employed to separate the distal most staple from the stack, to hold the remainder of the spring loaded stack, and may be used to feed the distal most staples into the staple forming mechanism. Feeding mechanisms of this type are found in U.S. Pat. No. 5,470,010 to Rothfuss et al., and in U.S. Pat. No. 5,582,616, also to Rothfuss et al.

Another hernia mesh attachment instrument uses a helical wire fastener that resembles a small section of spring. Multiple helical wire fasteners may be stored serially within the 5 mm shaft, and may be corkscrewed or rotated into tissue. A load spring may be used to bias or feed the plurality of helical fasteners distally within the shaft. A protrusion extends into the shaft to possibly prevent the ejection of the stack of fasteners by the load spring and may permit passage of a rotating fastener. Instruments and fasteners of these types are found in U.S. Pat. No. 5,582,616 to Bolduc et al., U.S. Pat. No. 5,810,882 to Bolduc et al., and in U.S. Pat. No. 5,830,221 to Stein et al.

Whereas the above surgical instruments may be used for hernia fastening applications, they use a spring mechanism to feed a plurality of fasteners through the surgical instrument. Spring mechanisms typically use a long soft coil spring to push a stack of fasteners through a guide or track within the shaft of the surgical instrument. These types of feeding mechanisms may be generally simple and reliable, but may require an additional secondary valving mechanism or protrusion to separate and feed one fastener from the stack.

Other surgical fasteners may be used for hernia mesh attachment but utilize either a reloadable single shot instrument or a rotary magazine that holds a small number of fasteners. These types of surgical fastening instruments can be found in U.S. Pat. Nos. 5,203,864 and 5,290,297, both to Edward Phillips. These instruments have not gained acceptance by the surgical community, possibly due to their single shot capabilities and the large size of the rotary magazine, which can restrict such an instrument to an open procedure.

Whereas all the above surgical instruments may be used for hernia fastening applications, they either use a spring mechanism to feed the plurality of fasteners through the surgical instrument, or a rotary magazine in lieu of a feeding mechanism. Other types of surgical fasteners may be available, such as surgical clips, and they can utilize feeding mechanisms that do not require the use of a spring to feed the clips distally. A reciprocating feeding mechanism is described in U.S. Pat. Nos. 5,601,573; 5,833,700; and U.S. Pat. No. 5,921,997 to Fogelberg et al. The Fogelberg et al. references teach a clip applier with a feeding mechanism that utilizes a reciprocating feed bar to feed a serial stack of clips. A feeder shoe may operably engage with and move with the distally moving feed bar and may slidingly engage with the proximally moving feed bar. Thus, the feeder shoe may index or push the stack of clips distally with the distally moving feed bar and remains stationary relative to the proximally moving feed bar. A valving mechanism may be also required to separate the distal-most clip from the stack and to hold the stack stationary as the distal most clip may be applied onto a vessel. Whereas the Fogelberg et al. references teach a reciprocating feeding mechanism with a single reciprocating member, they do not teach the use of the clip applier in the attachment of hernia mesh, nor do they teach the individual driving or feeding of each clip by a moving member.

U.S. Pat. No. 3,740,994 to DeCarlo Jr. describes a novel reciprocating feeding mechanism that may index a plurality of staples or clips, and may ready them for discharge by reciprocating one of a pair of opposing leaf spring assemblies. The staples reside serially within a guide rail with a fixed leaf spring assembly extending into the plane of the guide rail. A reciprocating leaf spring assembly may opposedly extend inwardly towards the fixed leaf spring assembly. As the reciprocating leaf spring assembly moves distally, each of individual leaf springs of the assembly may engage a staple and move it distally. The distally moving staples deflect the local individual leaf springs of the fixed leaf spring assembly, and the deflected leaf springs may return to the un-deflected position after passage of the staple. As the moving leaf spring assembly moves proximally, the leaf springs of the fixed leaf spring assembly hold the staples stationary and prevent proximal movement thereof. A secondary guide rail and valving mechanism may be provided to separate a single staple from the stack for forming and can hold the stack of staples stationary as the single clip is formed.

Additionally, similar feeding mechanisms are disclosed in U.S. Pat. No. 4,478,220 to DiGiovanni et al. and U.S. Pat. No. 4,471,780 to Menges et al. Both of these related patents teach a reciprocating feeding mechanism that uses one fixed member and one reciprocating member to feed or index a plurality of clips distally. Angled flexible fingers may be hingedly attached to the reciprocating member and operatively engage the clips when moving distally, and slidingly engage with the clips when moving proximally. The angled flexible fingers within the fixed member deflect out of the way when the clips move distally and spring up to stop proximal movement of the clip after the clip has passed. A secondary valving mechanism is also disclosed.

Commonly assigned U.S. Pat. No. 7,485,124, the disclosure of which is hereby incorporated by reference herein, teaches a device for delivering a plurality of individual surgical fasteners. In one embodiment, the delivery device includes a drive mechanism having distal and proximal ends. The drive mechanism has a moving member and a fixed opposing member, whereby the moving member is moveable proximally and distally with respect to the delivery device. The moving member has a sharpened distal end for piercing tissue. The device includes at least one surgical fastener located between the first and the second members. Each of the at least one surgical fasteners has a proximal end and a distal end. The device also has an actuator having at least two sequential positions. A first position for moving the moving member distally and piercing tissue, and a second position for moving the moving member proximally, thereby deploying the distal end of the fastener.

Tacks for fixing meshes used laparoscopically have generally been made of metal, such as stainless steel, nitinol, or titanium. The metal tacks were necessary to provide for sufficient holding strength, penetration of various prosthetic meshes, and for ease of manufacture. Until recently, there were no absorbable tacks available on the market, and surgeons could only use absorbable sutures in order to provide a fixation means that did not permanently stay in the body. However, using sutures is exceedingly difficult for laparoscopic procedures, and so they are generally not used unless the repair is done in an open fashion. With surgical trends leading to more minimally invasive techniques with minimum foreign body accumulation, an absorbable tack with minimum profile that can be applied laparoscopically is needed.

Commonly assigned U.S. Pat. No. 8,920,439, the disclosure of which is hereby incorporated by reference herein, discloses an applicator instrument for dispensing surgical fasteners having an elongated shaft with a proximal shaft section and a distal shaft section. The applicator instrument has an articulation controller coupled with the distal shaft section for selectively changing the angle between the distal shaft section and the proximal shaft section. The articulation controller has at least one flexible linkage extending through the shaft and has a proximal end connected with an actuator and a distal end connected with the distal shaft section. The actuator is mounted on a housing for sliding between proximal and distal ends of the housing for moving the at least one flexible linkage in proximal and distal directions. Surgical fasteners are disposed within elongated shaft for being dispensed one at a time from the distal end of the elongated shaft.

In spite of the above advances, intra-operative conditions during laparoscopic surgery remain challenging for the surgeon. There remains a need for applicator instruments for dispensing surgical fasteners that have improved ergonomics, that enable ipsilateral (same side) mesh tensioning, and that provide maneuverability both inside and outside of a body cavity. There also remains a need for applicator instruments for dispensing surgical fasteners at an angle relative to the primary axis of the instrument to allow for better access to the abdominal wall during ventral hernia surgery. In addition, there remains a need for applicator instruments that dispense surgical fasteners that effectively attach mesh to Cooper's ligament over a pubic bone. Although articulation is a potential solution to some of the above needs, it is desirable for a device that may address those needs without articulation. Such a device may have a simpler, more intuitive interface; a simpler, lower cost mechanism; and reduce the amount of torque experienced at the trocar site when using an articulating instrument.

SUMMARY OF THE INVENTION

In one embodiment, an applicator instrument for dispensing surgical fasteners includes a housing, a firing system disposed in the housing, and an actuator coupled with the housing for activating the firing system. In one embodiment, the applicator instrument includes an elongated shaft extending from the housing, the elongated shaft having a proximal end secured to the housing, a distal end, and a first axis extending between the proximal and distal ends, and one or more surgical fasteners disposed in the elongated shaft. In one embodiment, a distal end cap is secured to the distal end of the elongated shaft, the distal end cap having a surgical fastener dispensing window for dispensing the one or more surgical fasteners from the distal end cap. In one embodiment, the firing system has a firing rod that extends through the elongated shaft for dispensing the one or more surgical fasteners from the distal end cap. In one embodiment, the firing rod has a proximal section that moves along the first axis of the elongated shaft and a distal section that moves along a second axis that defines an angle with the first axis.

In one embodiment, the applicator instrument includes a plurality of surgical fasteners pre-loaded into the elongated shaft. In one embodiment, the pre-loaded surgical fasteners have lengths that extend along the first axis of the elongated shaft. In one embodiment, during a firing cycle, the firing system reorients a leading one of the pre-loaded surgical fasteners so that the length of the leading surgical fastener extends along the second axis for being dispensed from the distal end cap at an angle relative to the first axis.

In one embodiment, the proximal and distal sections of the firing rod are pivotally connected together. In one embodiment, the firing rod includes a joining member interconnecting the proximal section of the firing rod with the distal section of the firing rod. In one embodiment, the joining member has a proximal end that is pivotally connected with the proximal section of the firing rod and a distal end that is pivotally connected with the distal section of the firing rod. In one embodiment, the joining member is flexible and is rigidly connected to both the proximal and distal ends of the firing rod.

In one embodiment, the firing rod includes the proximal section, an extension of the proximal section, the joining member, and the distal section. In one embodiment, the proximal section and the extension of the proximal section are joined together and travel distally and proximally along a longitudinal axis $A_1$ during a firing cycle. In one embodiment, the joining member has a proximal end that is pivotally connected with a distal end of the extension of the proximal section of the firing rod and a distal end that is pivotally connected with a proximal end of the distal section of the firing rod. In one embodiment, the distal section of the firing rod includes an insertion fork having tines that are adapted to engage the respective legs of a surgical fastener.

In one embodiment, during an initial stage of a firing cycle, the proximal section of the firing rod and the joining member of the firing rod extend along the first axis and the distal shaft section of the firing rod extends along the second axis. In one embodiment, during a later stage of the firing cycle, the proximal section of the firing rod extends along the first axis, the distal section of the firing rod extends along the second axis that defines an angle relative to the first axis, and the joining member of the firing rod extends along a third axis that is nonparallel with the first axis and the second axis.

In one embodiment, the distal end cap has a surgical fastener dispensing window for dispensing surgical fasteners from the distal end of the elongated shaft. In one embodiment, the distal end cap includes an angled ramp that extends along the second axis for guiding movement of the distal section of the firing rod and the lead surgical fastener along the second axis when dispensing the lead surgical fastener from the distal end cap.

In one embodiment, the distal end cap has a top cap part and a bottom cap part that are assembled together. In one embodiment, the top cap part defines a ceiling of the angled ramp and the bottom cap part defines a floor of the angled ramp that collectively maintain the orientation of the distal shaft section as it moves in distal and proximal directions. In one embodiment, the surgical fastener dispensing window on the distal end cap is located at a distal-most end of the angled ramp and is bounded by the ceiling of the top cap part and the floor of the bottom cap part.

In one embodiment, the distal end cap has a curved ramp that extends between a proximal end and a distal end of the distal end cap. In one embodiment, the firing rod includes a flexible section that interconnects the proximal and distal sections of the firing rod so that the distal section of the firing rod is deflectable relative to the proximal section of the firing rod. In one embodiment, the curved ramp has a proximal section that is aligned with the first axis and a distal end that is aligned with the second axis.

In one embodiment, during an initial stage of a firing cycle the proximal and distal sections of the firing rod extend along the first axis, and during a later stage of the firing cycle the proximal section of the firing rod extends along the first axis, whereby the distal section of the firing rod extends along the second axis, and the flexible section of the firing rod is curved and extends through the curved ramp section of the distal end cap.

In one embodiment, the insertion fork has opposing tines adapted to engage the respective legs of the one or more surgical fasteners. In one embodiment, the opposing tines have C-shaped cross-sections with openings that oppose one another. In one embodiment, the tines have proximal ends with C-shaped cross-sections having openings that oppose one another and distal ends having L-shaped cross-sections having openings that oppose one another. In one embodiment, the tines having lengths with L-shaped cross-sections having openings that oppose one another. In one embodiment, the tines having L-shaped cross sections facilitate loading surgical fasteners between the tines, particularly when surgical fasteners are advanced distally at one level and then shifted into alignment with the tines for being loaded onto an insertion fork.

In one embodiment, the distal section of the firing rod includes an insertion fork having opposing tines adapted to engage the one or more surgical fasteners. In one embodiment, the tines are moveable between an open position in which the tines are further apart and a closed position in which the tines are closer together. In one embodiment, the insertion fork includes a spring providing a force that normally urges the opposing tines into the open position, and the applicator instrument has a cam surface that engages the insertion fork during a firing cycle for overcoming the force of the spring and urging the tines into the closed position. In one embodiment, the spring normally closes the tines and the cam surface opens the tines.

In one embodiment, the distal end cap has a top surface and a distal end face that extends within a plane that is perpendicular to the second axis. In one embodiment, the top surface of the distal end cap has a first set of spaced protrusions and the distal end face has a second set of spaced protrusions.

In one embodiment, the distal end cap has a first section having a first color and a second section having a second color that contrasts with the first color to define a color contrasting boundary that provides visual indicators of the orientation of the distal end cap and the location of the surgical fastener delivery window. In one embodiment, the color contrasting boundary is aligned with the second axis that indicates the dispensing angle of the surgical fasteners. In one embodiment, the color contrasting boundary defines an arrow that points to the surgical fastener dispensing window. In one embodiment, the arrow is aligned with the second axis.

In one embodiment, an applicator instrument for dispensing surgical fasteners includes a housing, a firing system disposed within the housing, and an actuator coupled with the housing for activating the firing system. In one embodiment, the applicator instrument has an elongated shaft extending from the housing, the elongated shaft having a proximal end secured to the housing, a distal end, and a first axis extending between the proximal and distal ends, surgical fasteners disposed in the elongated shaft, and a distal end cap secured to the distal end of the elongated shaft, the distal end cap having a surgical fastener dispensing window for dispensing the surgical fasteners from the distal end cap.

In one embodiment, the firing system includes a firing rod that extends through the elongated shaft for dispensing the surgical fasteners one at a time from the distal end cap. In one embodiment, the firing rod has a proximal section, a distal section, and a joining member having a proximal end pivotally connected with the proximal section of the firing rod and a distal end pivotally connected with the distal section of the firing rod. In one embodiment, during an initial stage of a firing cycle, the proximal section and the joining member of the firing rod extend along the first axis and the distal shaft section extends along the second axis. In one embodiment, during a later stage of the firing cycle, the proximal section of the firing rod extends along the first axis, the distal section of the firing rod extends along the second axis that is angled relative to the first axis, and the joining member extends along a third axis that is nonparallel with the first axis and the second axis.

In one embodiment, a plurality of surgical fasteners are pre-loaded into the elongated shaft. The pre-loaded surgical fasteners have lengths that extend along the first axis. In one embodiment, between an initial stage and a later stage of the firing cycle, the firing system reorients a leading one of the pre-loaded surgical fasteners from the first axis to the second axis so that the length of the leading surgical fastener extends along the second axis for being dispensed from the distal end cap.

In one embodiment, the distal end cap has a top cap part and a bottom cap part that are assembled together. In one embodiment, the top cap part defines a ceiling of the angled ramp and the bottom cap part defines a floor of the angled ramp, whereby the surgical fastener dispensing window is located at a distal-most end of the angled ramp and is bounded by the ceiling of the top cap part and the floor of the bottom cap part. In one embodiment, the exterior face of the cap is sloped to be perpendicular to the angled ramp. Thus, when the device is preloaded, mesh and tissue conform to this exterior face to allow for a perpendicular approach of straps into tissue.

In one embodiment, a method of repairing a hernia defect includes inserting a mesh into a patient's abdominal cavity, placing the mesh over a hernia defect, and providing an applicator instrument for dispensing surgical fasteners. In one embodiment, the applicator instrument includes a housing, a firing system disposed in the housing, an actuator coupled with the housing for activating the firing system, an elongated shaft extending from the housing, the elongated shaft having a proximal end secured to the housing, a distal end, and a first axis extending between the proximal and distal ends, one or more surgical fasteners disposed in the elongated shaft, a distal end cap secured to the distal end of the elongated shaft, the distal end cap having a surgical fastener dispensing window for dispensing the one or more surgical fasteners from the distal end cap, the firing system including a firing rod that extends through the elongated shaft for dispensing the one or more surgical fasteners from the distal end cap, wherein during a firing cycle the firing rod has a proximal section that moves along the first axis of the elongated shaft and a distal section that moves along a second axis that defines an angle with the first axis. In one embodiment, the method includes inserting the distal end of the elongated shaft into the patient's abdominal cavity, abutting the distal end cap against the mesh and engaging the actuator for dispensing one of the surgical fasteners through the mesh and into an abdominal wall of the patient.

In one embodiment, the pre-loaded surgical fasteners have lengths or primary axes that have the same orientation as the elongated axis (e.g., axis $A_1$) of the elongated shaft.

In one embodiment, the surgical fasteners are positioned in the elongated shaft so that their respective primary axes are substantially the same as the secondary axis (e.g., Axis A2) of the surgical fastener dispensing window.

In one embodiment, the angular displacement of the secondary axis A2 relative to the first axis $A_1$ is between about 10-45 degrees.

In one embodiment, the distal end cap has protrusions provided adjacent the surgical fastener dispensing window for releasably engaging surgical mesh for manipulating the surgical mesh and holding the surgical mesh in place during a firing cycle. In one embodiment, the protrusions extend radially outward and/or axially from the distal end face of the distal end cap.

In one embodiment, the distal section of the firing rod engages with a surgical fastener and rotates the surgical fastener from a first position along the primary axis of the elongated shaft to a second position along the secondary axis of the surgical fastener dispensing window.

In one embodiment, the joining member is positioned between the proximal and distal sections of the firing rod. In one embodiment, the distal end cap has a central opening provided therein for enabling displacement of the joining member during a firing cycle. In one embodiment, when the firing rod is fully extended for dispensing a surgical fastener from the distal end cap, the proximal section of the firing rod extends along a first axis, the distal section of the firing rod extends along a second axis that defines an angle with the first axis, and the joining member extends along a third axis that is nonparallel with the first axis and nonparallel with the second axis.

In one embodiment, the housing has a hand grip that extends along an axis that defines an angle with the first axis of the elongated shaft. In one embodiment, the angle of the hand grip with the first axis is about 15-25 degrees and more preferably about 20 degrees. In one embodiment, the angle of the hand grip relative to the first axis of the elongated shaft may be adjustable.

Although the present invention is not limited by any particular theory of operation, it is believed that providing an applicator instrument as disclosed herein may reduce the amount of force required to deliver and dispense a surgical fastener for securing a prosthetic device to tissue, which allows for a tighter curved geometry and/or a more acute delivery angle.

In one embodiment, the applicator instrument enables surgical fasteners to be dispensed at an angle, which provides for better access to the abdominal wall during ventral hernia surgery.

In one embodiment, the above-noted improved access, coupled with an enhanced handle will improve the ergonomics of the procedure, thereby allowing the user to torque the device instead of pushing the device against tissue.

In one embodiment, changing the dispensing angle of the surgical fasteners eliminates the need to change the angle of the angle of the distal end of the shaft (e.g., articulation), which may minimize complexity and cost, and reduce the length of surgical procedures.

In one embodiment, the applicator instrument disclosed herein may be used during laparoscopic inguinal hernia repairs to secure Cooper's ligament to a public bone. During surgical procedures, it is often desirable to deliver a fixation point directly over Cooper's ligament. However, directly beneath the ligament is the rigid pubic bone. Because the ligament is very thin (~1-3 mm), it is difficult to deliver fasteners directly onto the ligament. However, the applicator instrument disclosed herein enables surgical fasteners to be delivered at an angle relative to the tissue, whereby the surgical fasteners will scythe across the pubis and secure the mesh to Cooper's ligament more effectively, without damaging the fasteners or the delivery device.

These and other preferred embodiments of the present invention will be described in more detail below.

BRIEF DESCRIPTION OF THE DRAWING

FIG. 5 shows the top cap part and the bottom cap part shown in FIG. 2.

FIGS. 12A-1 through 12C-1 show a firing system of the applicator instrument during the firing cycle shown in FIGS. 12A-120.

FIG. 16 shows an exploded view of an applicator instrument for dispensing surgical fasteners including an elongated shaft, a firing rod having a flexible section, and a distal end cap, in accordance with one embodiment of the present invention.

FIGS. 17A and 17B show the distal end of the firing rod shown in FIG. 16.

FIG. 18 shows an applicator instrument having an elongated shaft and a distal end cap having a curved ramp, in accordance with one embodiment of the present invention.

FIGS. 19E-1 and 19E-2 show perspective and side views of the applicator instrument shown in FIG. 19E.

FIG. 27C-1 shows a perspective view of the applicator instrument shown in FIG. 27C.

FIGS. 30A-300 show an applicator instrument including a distal end cap having projections, in accordance with one embodiment of the present invention.

DETAILED DESCRIPTION

Figure 1:
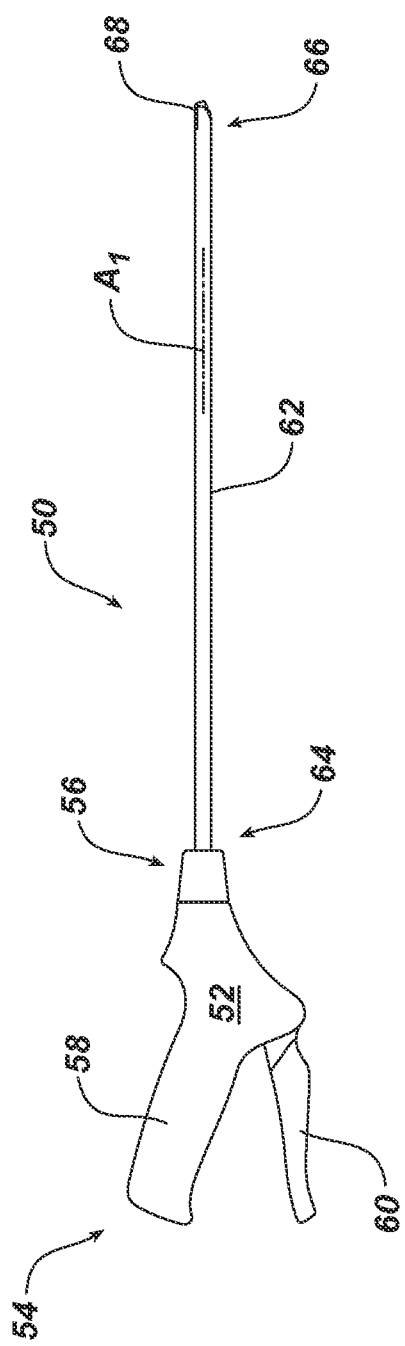
FIG. 1 shows a side elevation view of an applicator instrument for dispensing surgical fasteners including a housing, an actuator, an elongated shaft, and a distal end cap, in accordance with one embodiment of the present invention.

Referring to FIG. 1, in one embodiment, an applicator instrument 50 for dispensing surgical fasteners includes a housing 52 having a proximal end 54 and a distal end 56. The housing 52 includes a handle 58. A trigger 60 is coupled with the housing 52 for activating a firing system that dispenses surgical fasteners as will be described in more detail herein.

In one embodiment, the applicator instrument 50 has an elongated shaft 62 with a proximal end 64 connected with the distal end 56 of the housing 52 and a distal end 66 remote therefrom. In one embodiment, the elongated shaft 62 is substantially straight and extends along a longitudinal axis $A_1$. The applicator instrument 50 has a distal end cap 68 secured to the distal end 66 of the elongated shaft 62. The distal end cap 68 is designed to dispense a surgical fastener that is off-axis or angled relative to the longitudinal axis $A_1$ of the elongated shaft 62.

Figure 19A:
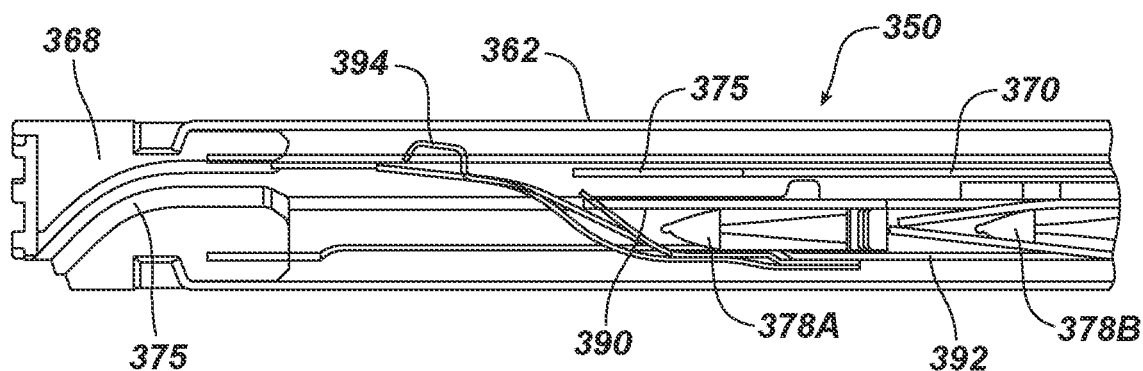
FIGS. 19A-19E show a method of using an applicator instrument having a distal end cap with a curved ramp, in accordance with one embodiment of the present invention.
Figure 19B:
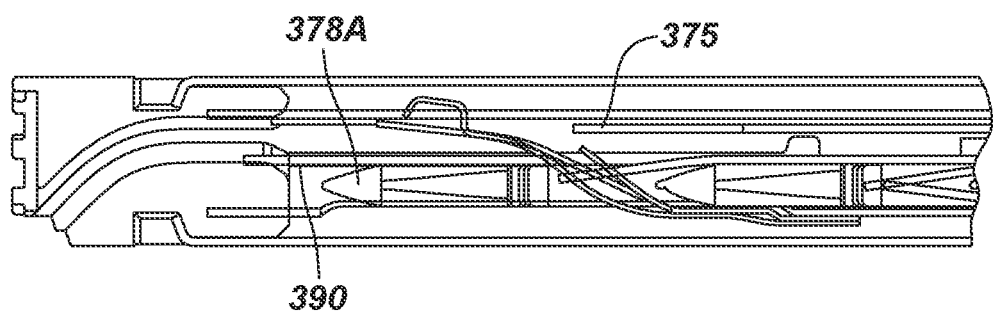
Figure 19C:
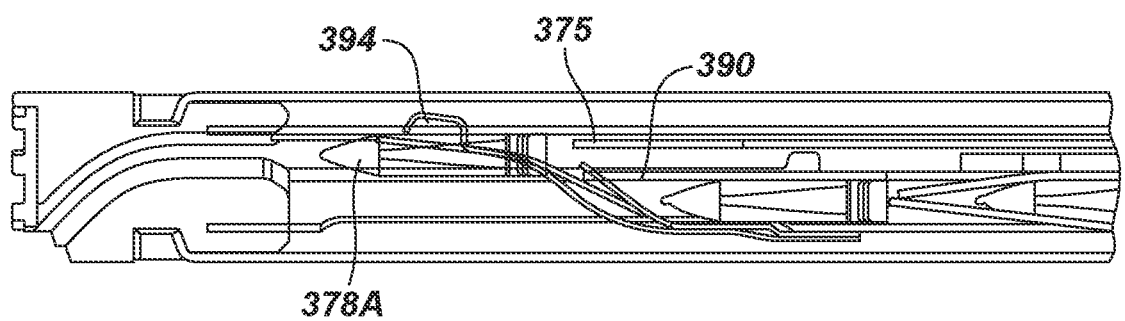
Figure 19D:
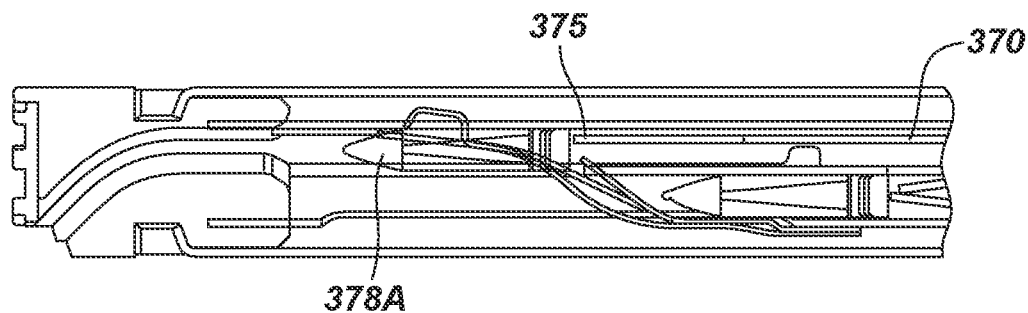
Figure 19E:
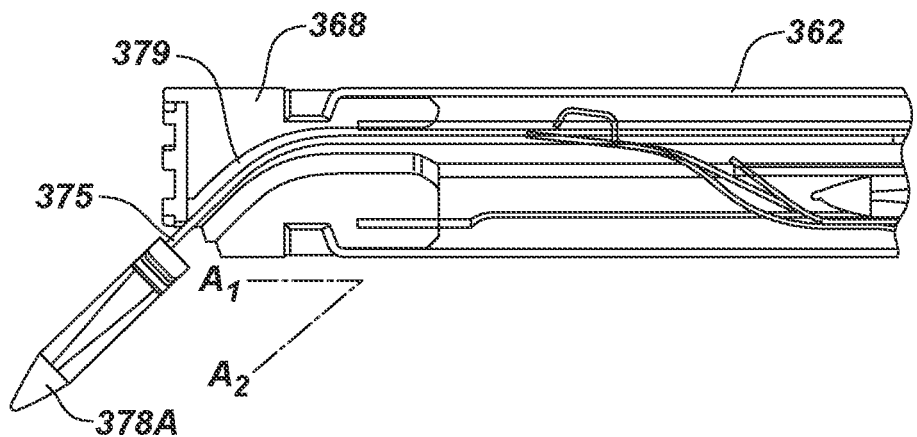
Figures 1, 19E:
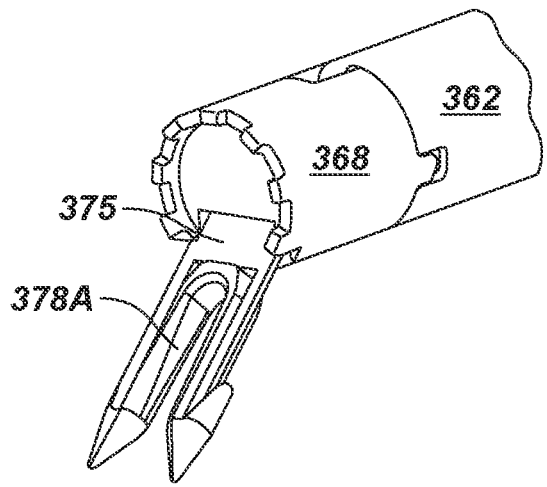
Figures 2, 19E:
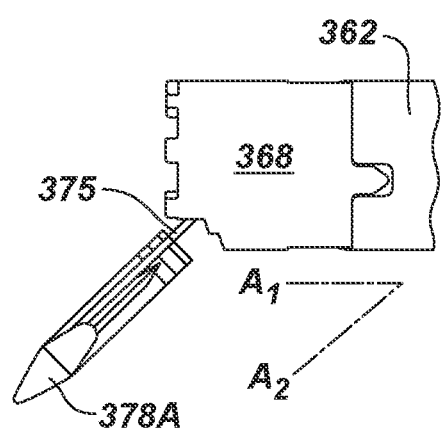
FIG. 2 shows an exploded view of the distal end of the applicator instrument shown in FIG. 1 including the elongated shaft, a firing rod having a proximal section, a joining member and a distal section, the distal end cap including a top cap part and a bottom cap part, a surgical fastener, and a firing rod insert, in accordance with one embodiment of the present invention.

Referring to FIG. 2, in one embodiment, the applicator instrument 50 includes the elongated shaft 62 having the distal end 66. In one embodiment, the elongated shaft 62 has a tubular shape and includes an elongated conduit that extends from the proximal end to the distal end 66 thereof. In one embodiment, the firing system is disposed inside the housing 52 (FIG. 1) and extends through the elongated conduit of the elongated shaft 62. In one embodiment, the firing system includes a firing rod having a proximal section 70 with an extension 72, a joining member 74, and a distal section 76 including an insertion fork 75 having tines 77A, 77B that are adapted for dispensing a surgical fastener 78 from the distal end 66 of the elongated shaft 62.

In one embodiment, the proximal section 70 of the firing rod and the extension 72 of the proximal section of the firing rod are connected together and are adapted to move together, in distal and proximal directions along the axis $A_1$. The proximal section 70 of the firing rod has one or more openings 80A formed therein that are adapted to receive a spacer projection 81 on an underside of a spacer 82. In one embodiment, the spacer 82 is made of plastic or metal and is adapted to constrain movement of the proximal section 70 and the extension 72 of the proximal section of the firing rod within the elongated conduit so that the proximal section and the extension of the firing rod move along the longitudinal axis $A_1$. In one embodiment, the extension 72 of the proximal section of the firing rod has one or more openings 80B that are adapted to receive spacers 82 similar to those described above.

In one embodiment, the extension 72 of the proximal section of the firing rod has a distal end 84 with a distal pivot connection 86. The joining member 74 has a proximal end 88 with a proximal pivot connection 90 for pivotally connecting the distal end 84 of the extension 72 with the proximal end 88 of the joining member 74. In one embodiment, the joining member 74 has a distal end 92 with a distal pivot connection 94, and the distal section 76 of the firing rod has a proximal end 96 with a proximal pivot connection 98 for pivotally connecting the distal end 92 of the joining member 74 with the proximal end 96 of the distal section 76 of the firing rod.

In one embodiment, the distal end cap 68 is secured to the distal end 66 of the elongated shaft 62. In one embodiment, the distal end cap 68 includes a top cap part 100 that defines a ceiling for the surgical fastener 78 being dispensed from the distal end 66 of the elongated shaft 62 and a bottom cap part 102 that defines a floor for the surgical fastener being dispensed from the distal end of the elongated shaft. In one embodiment, the distal end cap 68 is made of molded plastic and the top and bottom cap parts 100, 102 are connected together.

Figure 3:
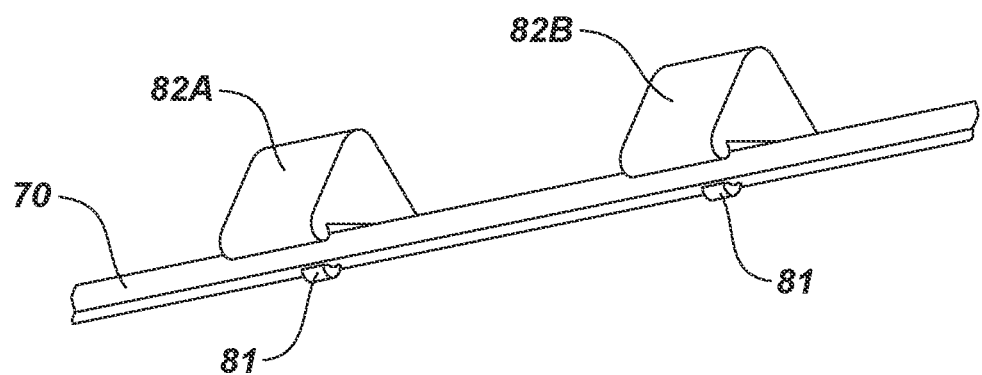
FIG. 3 shows the firing rod of FIG. 2 and two inserts assembled with the firing rod, in accordance with one embodiment of the present invention.

Referring to FIG. 3, in one embodiment, the proximal section 70 of the firing rod has two or more spacers 82A, 82B secured thereto and are spaced from one another along the length of the proximal section 70. The spacers are secured to the proximal section 70 using spacer projections 81. Although two spacers 82 are shown in FIG. 3, in other embodiments one or more spacers may be secured to the proximal section 70 and the extension 72 of the firing rod 70.

Referring to FIGS. 4A-4D, in one embodiment, the distal end 66 of the elongated shaft 62 is designed for having the distal end cap 68 (FIGS. 1 and 2) secured thereto. In one embodiment, the distal end 66 of the elongated shaft 62 has a top side 104 having an upper cutout 106 adapted to seat a proximal end of the top cap part 100 (FIG. 2) of the distal end cap, and a lower end 108 having a lower cutout 110 adapted to seat the bottom cap part 102 (FIG. 2) of the distal end cap. In one embodiment, the distal end 66 of the elongated shaft 62 includes a first lateral wall 112 that extends between the upper end 104 and the lower end 108, and an opposing second lateral wall 114 that also extends between the upper end 104 and the lower end 108. The first lateral wall 112 has a first securing flange 116 located at a lower end thereof and the second lateral wall 114 has a second securing flange 118 located at a lower end thereof. The first and second securing flanges 116, 118 are adapted to engage notches on the lateral sides of the bottom cap part 102 for securing the bottom cap part to the distal end 66 of the elongated shaft 62. In one embodiment, the respective lower edges of the opposing first and second lateral walls 112, 114 define sloping surfaces that slope upwardly toward the distal most ends of the first and second lateral walls.

Referring to FIGS. 2 and 5, in one embodiment, the distal end cap 68 includes the top cap part 100 and the bottom cap part 102 that are adapted to be assembled together and secured to the distal end 66 of the elongated shaft 62. As will be described in more detail herein, the top cap part 100 defines a ceiling and the bottom cap part 102 defines a floor for the surgical fasteners as they are dispensed from the distal end of the elongated shaft 62. In one embodiment, the top and bottom cap parts 100, 102 have internal surfaces that engage the distal section 76 of the firing rod and/or the surgical fastener 78 loaded onto the distal section to provide positive control over the orientation and the position of the surgical fastener as it is dispensed from the distal end of the applicator instrument.

Figure 6A:
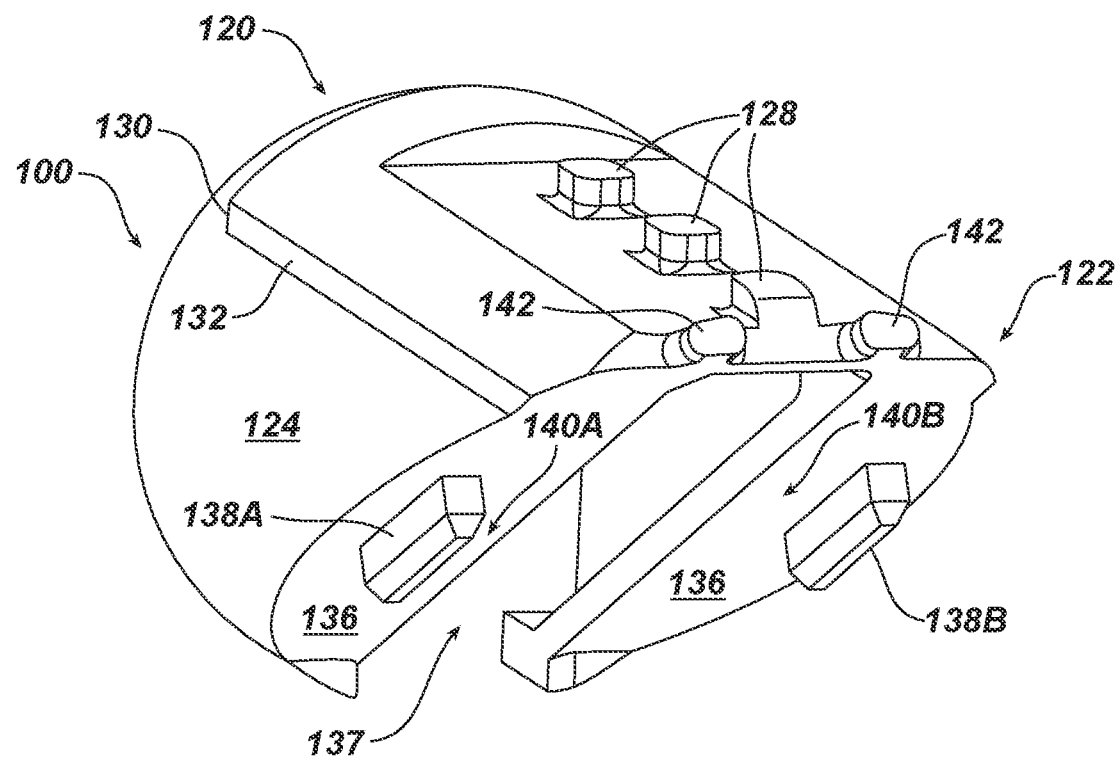
FIGS. 6A-6C show the top cap part shown in FIGS. 2 and 5.
Figure 6B:
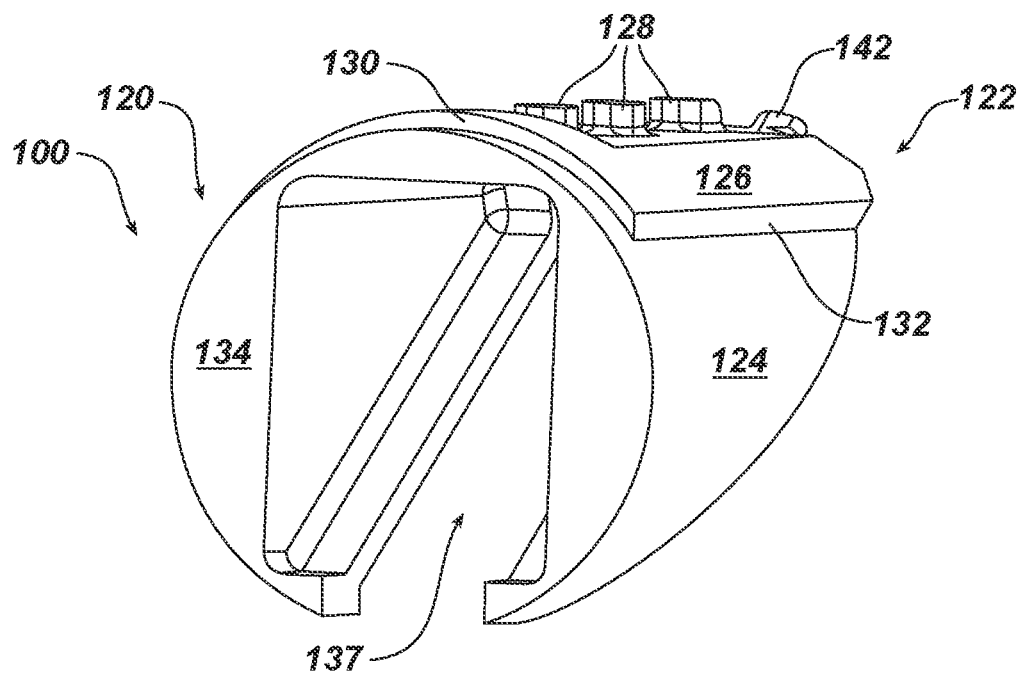
Figure 6C:
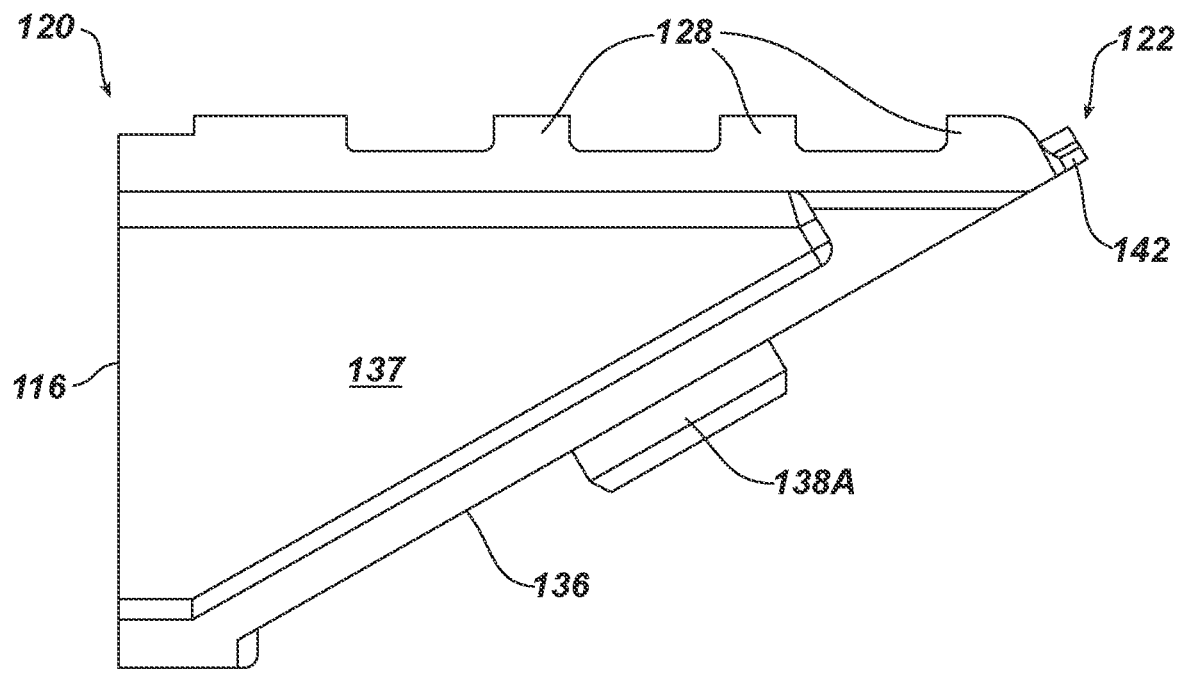

Referring to FIGS. 6A-6C, in one embodiment, the top cap part 100 has a proximal end 120 that is secured to the distal end of the elongated shaft and a distal end 122 that defines a distal-most end of the applicator instrument. The top cap part 100 has an outer wall 124 having a tubular shape and a base 126 for a first set of gripping features 128 (e.g., projections) located on the top side of the top cap part 100. The base 126 is elevated relative to the outer surface of the outer wall 124 to define a rear stop surface 130 and lateral stop surfaces 132. Referring to FIGS. 6A-6B and 4A-4B, when the top cap part 100 is secured to the distal end 66 of the elongated shaft 62, the rear stop surface 130 and the lateral stop surfaces 132 engage the proximal end and lateral sides of the upper cutout 106 to properly orient the top cap part 100 relative to the elongated shaft 62 and to prevent the top cap part from moving and/or shifting relative to the distal end 66 of the elongated shaft 62.

Referring to FIGS. 6A-6C, in one embodiment, the top cap part 100 has a proximal face 134 and a sloping bottom surface 136 that slopes upwardly between the proximal face 134 and the distal end 104. The sloping bottom surface 136 defines the ceiling that guides sliding movement of the distal section 76 of the firing rod (FIG. 2) as the distal section of the firing rod moves distally through the distal end cap for dispensing a surgical fastener. The top cap part 100 has a central opening 137 that extends from the proximal face 134 to the distal end 104. In one embodiment, the central opening 137 provides a space for the joining member 74 and the proximal end 96 of the distal section 76 of the firing rod to move (e.g., pivot or shift upwardly) as surgical fasteners are dispensed from the distal end cap 68 (FIG. 2).

Referring to FIGS. 6A and 6C, in one embodiment, the top cap part 100 includes a pair of projections 138A, 138B that extend from the sloping bottom surface 136 for forming a connection with the bottom cap part 102 (FIG. 2). The sloping bottom surface 136 extends around the projections 138A, 138B and has interior regions 140A, 140B that extend between the projections. In one embodiment, the interior regions 140A, 140B define the ceiling on the top cap part 100 that controls the movement and orientation of the distal section 76 of the firing rod. The projections 138A, 138B are used to form a snap-fit connection with the bottom cap part 102 (FIG. 5).

Referring to FIGS. 6A-6C, in one embodiment, the top cap part 100 has a second set of gripping features 142 that are located at the distal most end of the top cap part 100 for gripping and engaging mesh that opposes a distal most end of the applicator instrument.

Figure 7A:
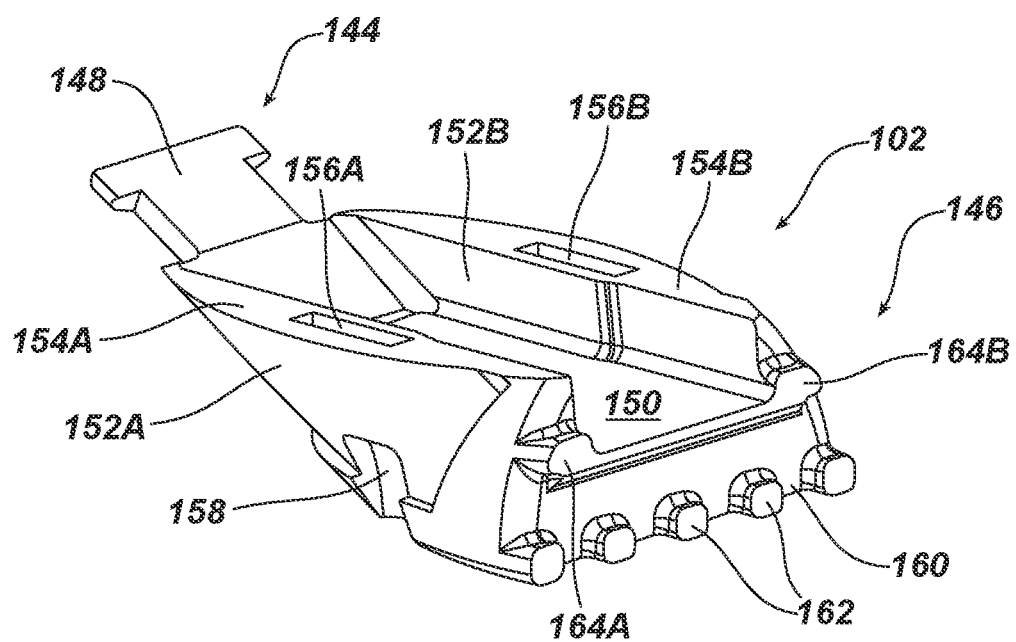
FIGS. 7A-7C show the bottom cap part shown in FIGS. 2 and 5.
Figure 7B:
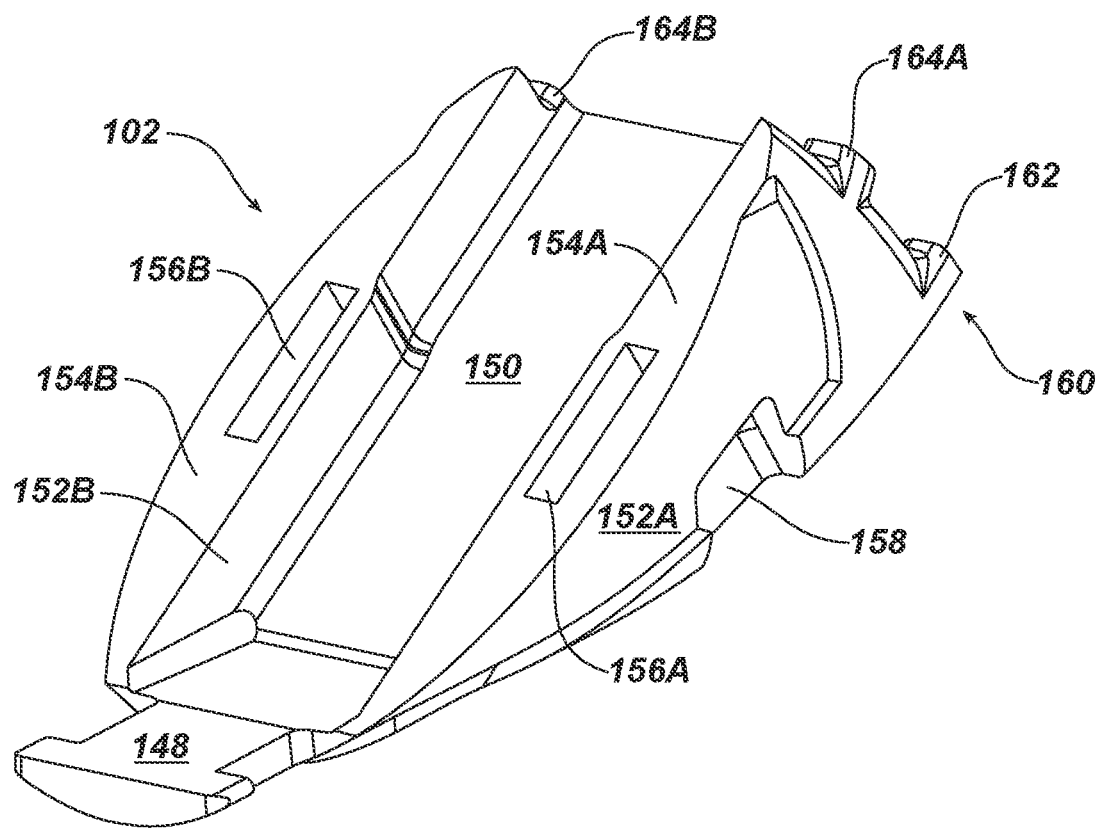
Figure 7C:
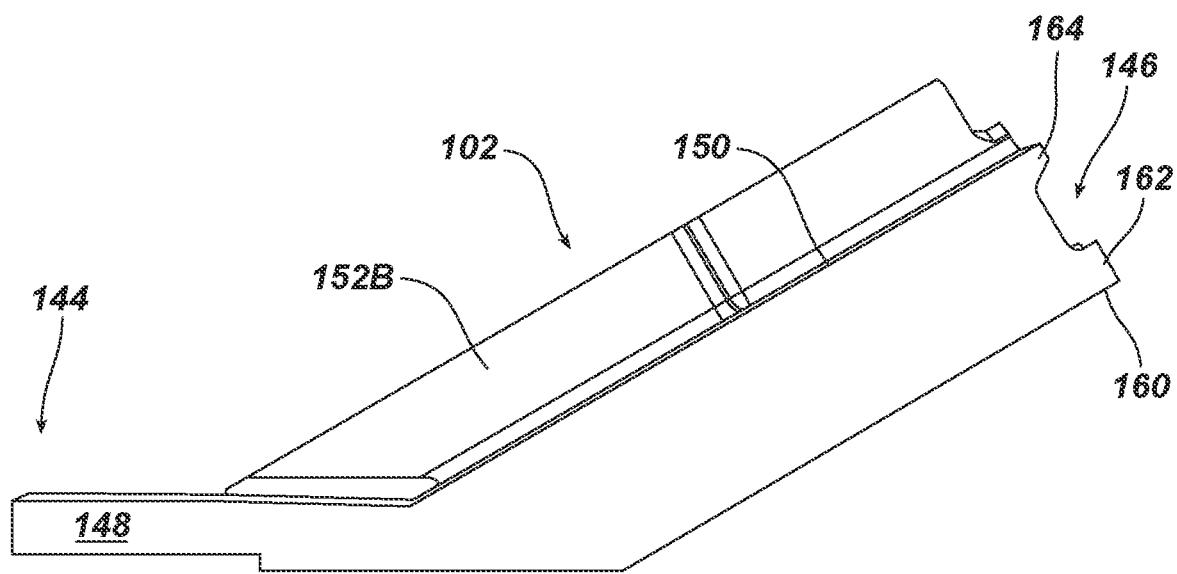

Referring to FIGS. 7A-7C, in one embodiment, the bottom cap part 102 has a proximal end 144 and a distal end 146. The proximal end 144 of the bottom cap part includes a keying feature 148 that that constrains the bottom cap part 102 with the lower cutout 137 at the distal end 166 of the elongated shaft 62 (FIGS. 4B and 4C) for securing the bottom cap part to the elongated shaft.

In one embodiment, the bottom cap part has a sloping floor 150 that slopes upwardly between the proximal end 144 and the distal end 146 for guiding the distal section 76 of the firing rod as it moves distally through the distal end cap 68. The sloping floor 150 is bounded by opposing lateral walls 152A, 152B having upper ends 154A, 154B with respective slots 156A, 156B that are adapted to receive the projections 138A, 138B of the upper cap part 100 (FIG. 6A) when the upper and bottom cap parts are assembled together and secured to the distal end of the elongated shaft.

Figure 4A:
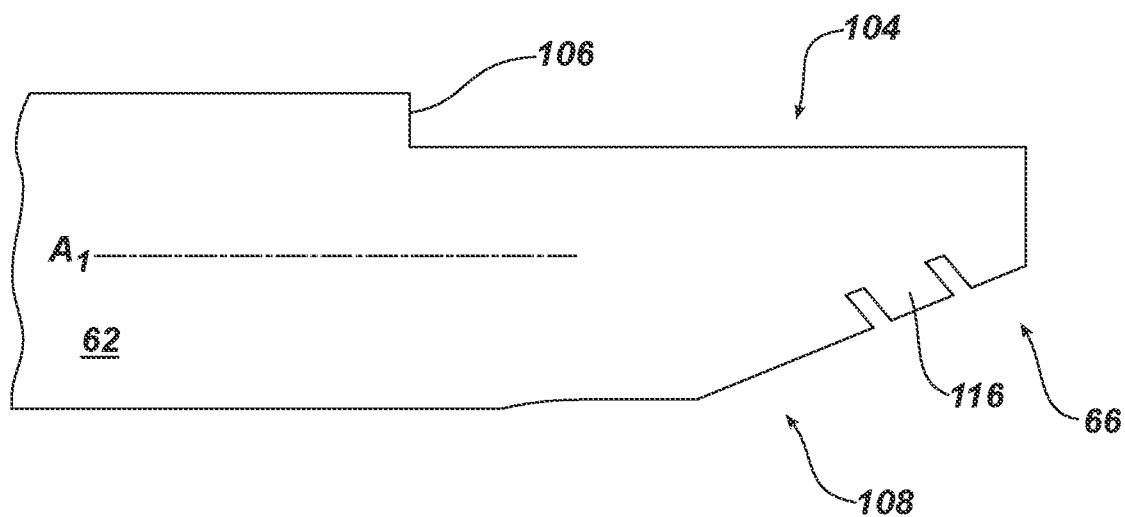
FIGS. 4A-4D show the distal end of the elongated shaft shown in FIGS. 1 and 2.
Figure 4B:
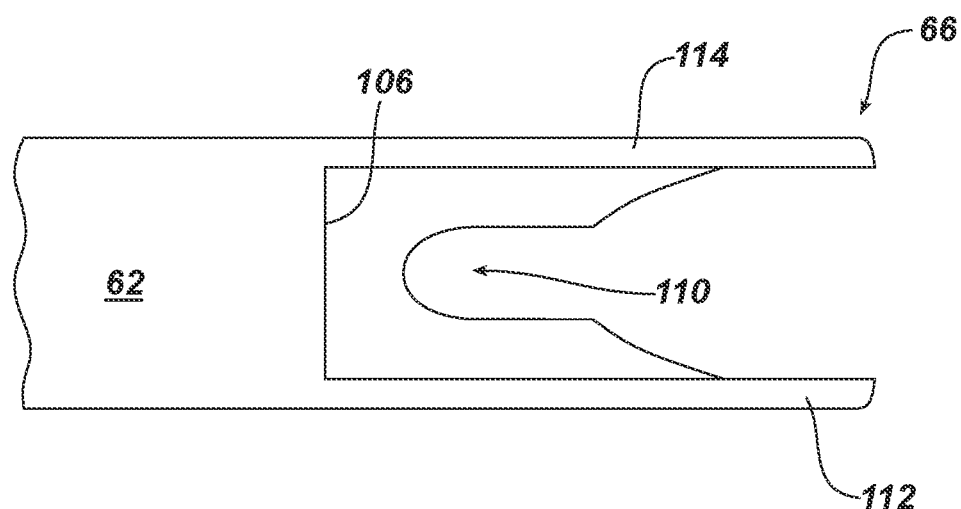
Figure 4C:
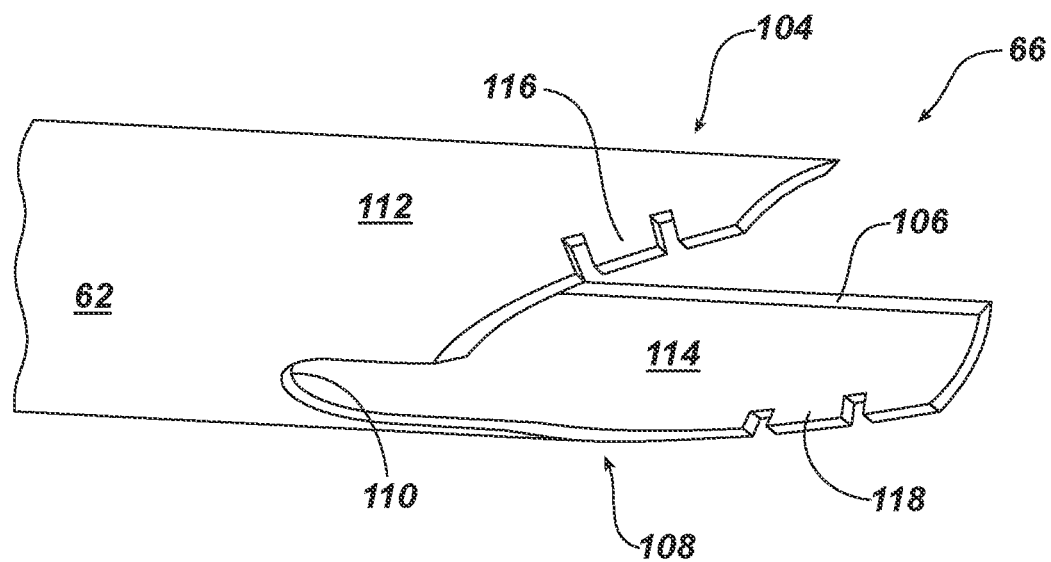
Figure 4D:
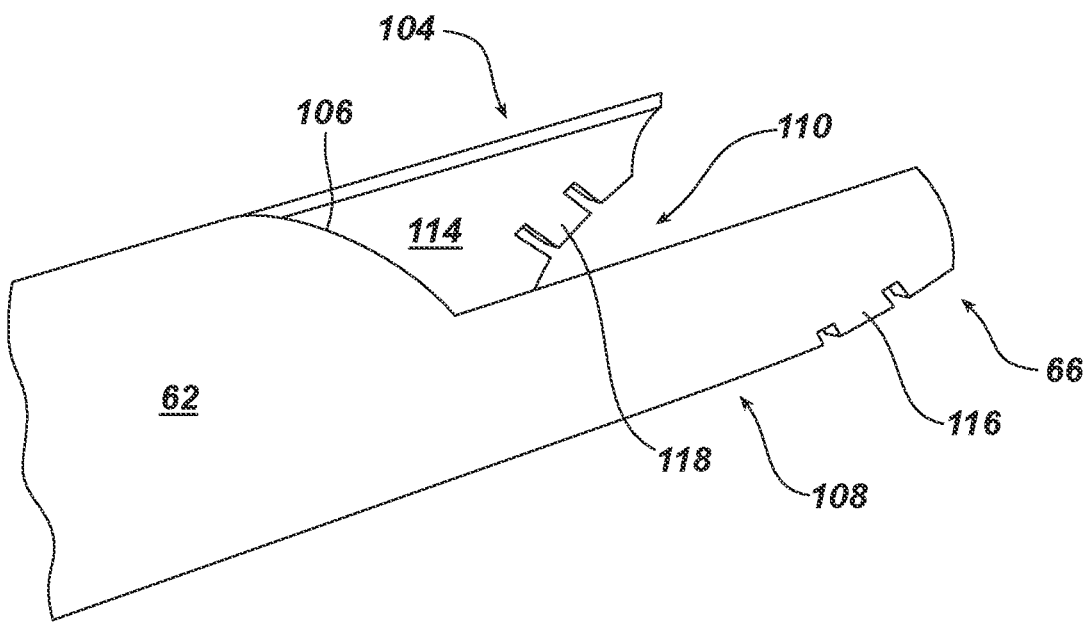

In one embodiment, each of the opposing lateral walls 152A, 152B has a notch 158 formed in an outer lateral surface thereof. Referring to FIGS. 4C-4D and 7A-7B, in one embodiment, the securing flanges 116, 118 at the distal end 66 of the elongated shaft 62 are inserted into notches 158 on the opposing lateral walls 152A, 152B of the bottom cap part 102 for securing the bottom cap part to the elongated shaft 62. The engagement of the securing flanges of the shaft with the notches of the bottom cap part 102 serves to properly orient the bottom cap part relative to the shaft and prevents the bottom cap part from moving relative to the shaft. This engagement also holds the bottom cap part and the top cap part together and constrains the top cap part 100 by biasing the rear stop 130 in the top cap part 100 (FIG. 6B) against the cutout 106 in the distal end 66 of the elongated shaft 62 (FIG. 4D).

Referring to FIGS. 7A-7C, in one embodiment, the distal end 146 of the bottom cap part 102 has a lower edge 160 having a first set of gripping features 162 that are spaced from one another and that extend laterally along the lower edge 160. In one embodiment, the bottom cap part 102 has a second set of gripping features 164A, 164B that are located above the first set of gripping features 162. In one embodiment, a first one 164A of the second set of gripping features is aligned with the first lateral wall 152A and a second one 164B of the second set of gripping features is aligned with the second lateral wall 152B. In one embodiment, the second set 164A, 164B of gripping features are located adjacent the distal-most end of the sloping floor 150. The gripping features are adapted to engage an opposing surgical mesh for positioning the mesh and preventing the mesh from moving relative to the applicator instrument as surgical fasteners are dispensed from the instrument.

Figure 8A:
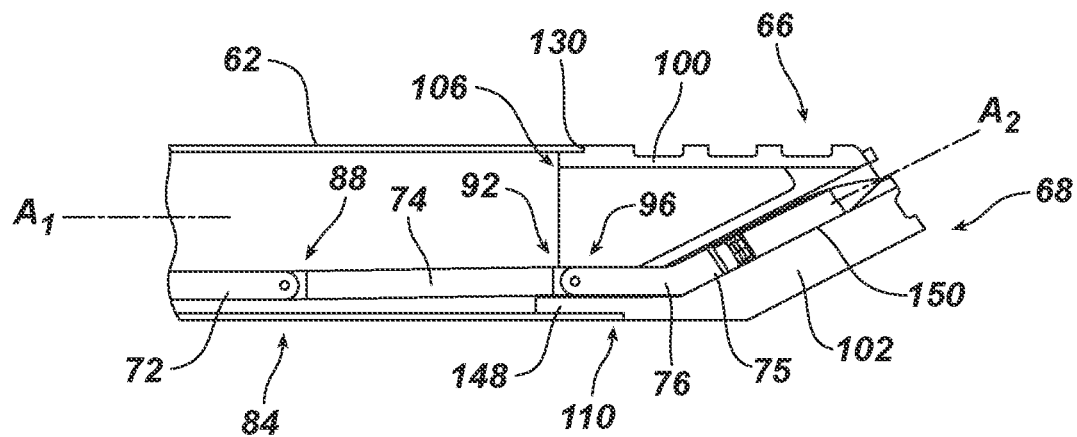
FIGS. 8A-8C show the distal end of an applicator instrument for dispensing surgical fasteners, in accordance with one embodiment of the present invention.
Figure 8B:
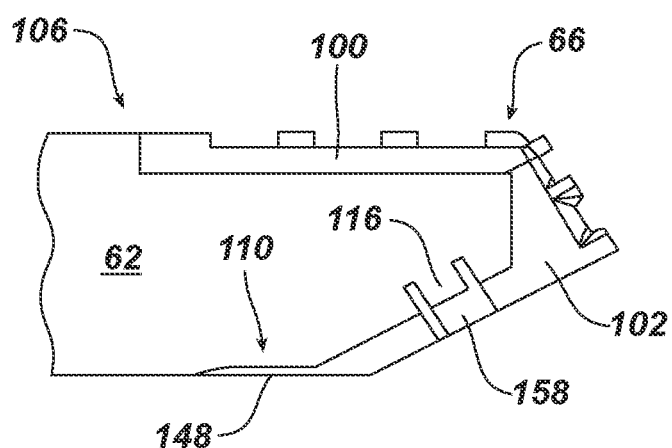
Figure 8C:
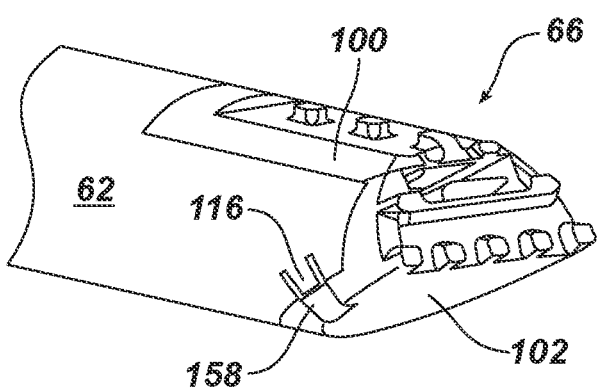

Referring to FIGS. 8A-8C, in one embodiment, the top cap part 100 and the bottom cap part 102 are assembled together to form the distal end cap 68, and the distal end cap is secured to the distal end 66 of the elongated shaft 62. Referring to FIGS. 4A-4D and 8A-8C, in one embodiment, the rear stop 130 of the elevated base 126 of the top cap part 100 engages the top cutout 106 at the distal end 66 of the elongated shaft 62, the keying feature 148 of the bottom cap part 102 engages the lower cutout 110 at the distal end 66 of the elongated shaft 62, and the securing flanges 116, 118 at the distal end 66 of the elongated shaft 62 engage the notches 158 of the bottom cap part 102 for securing the distal end cap 68 to the distal end 66 of the elongated shaft 62 and for properly orienting the distal end cap relative to the elongated shaft.

Referring to FIG. 8A, when the distal end cap 68 is secured to the distal end 66 of the elongated shaft 62, the sloping bottom surface 136 of the top cap part 100 and the sloping floor 150 of the bottom cap part 102 extend along an axis $A_2$ that defines an obtuse angle of about 25-35 degrees relative to the longitudinal axis $A_1$ of the elongated shaft 62. The sloping bottom surface 136 of the top cap part defines a ceiling that positively controls movement of the insertion fork 75 to ensure that the distal section of the firing rod moves along the axis $A_2$. The sloping floor 150 of the bottom cap part opposes the sloping bottom surface 136 of the top cap part and also positively controls distal movement of the distal section of the firing rod to ensure that the insertion fork moves along the axis $A_2$. As used herein, the term distal section of the firing rod may also be referred to as an insertion fork having opposing tines that engage a surgical fastener.

In one embodiment, the extension 72 of the proximal section 70 of the firing rod is adapted to move in distal and proximal directions along the longitudinal axis $A_1$. The distal end 84 of the extension 72 is pivotally connected to the proximal end 88 the joining member 74. In turn, the distal end 92 of the joining member 74 is pivotally connected to the proximal end 96 of the distal section 76 of the firing rod.

Figure 9A:
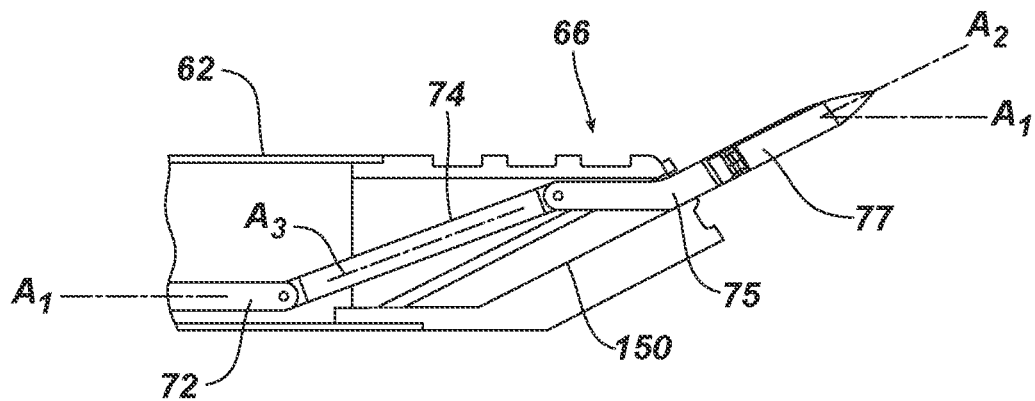
FIGS. 9A-9C show the distal end of the applicator instrument of FIGS. 8A-8C when dispensing a surgical fastener, in accordance with one embodiment of the present invention.
Figure 9B:
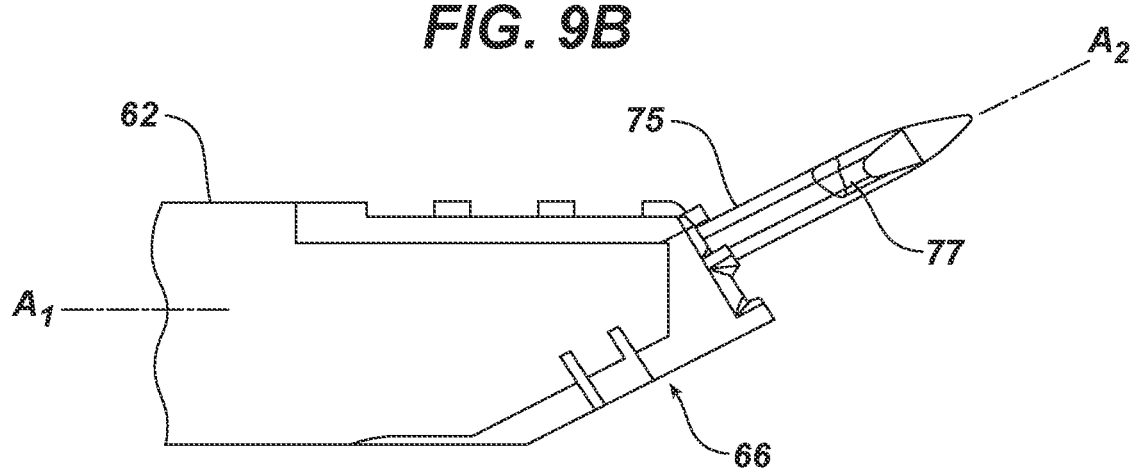
Figure 9C:
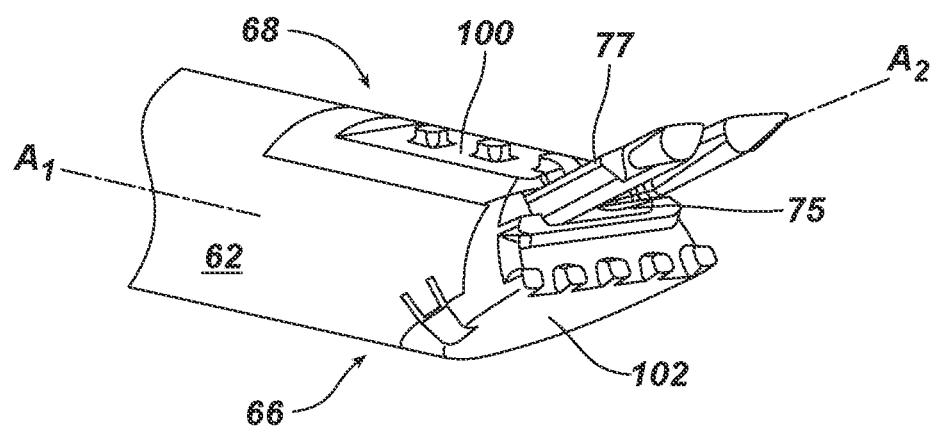

Referring to FIGS. 9A-9C, during a firing cycle, the extension 72 moves distally along the axis $A_1$ toward the distal end 66 of the elongated shaft 62. The sloping bottom surface 136 (FIG. 6A) of the top cap part 100 and the sloping floor 150 of the bottom cap part 102 positively control the orientation and distal movement of the distal section 76 of the firing rod relative to the axis $A_1$ of the elongated shaft 62 so that the tines 77 of the insertion fork 75 can only move along the axis $A_2$. The pivot connections at the proximal and distal ends of the joining member 74 enable the insertion fork 75 to maintain the orientation shown in FIG. 9A as the insertion fork moves from the position shown in FIG. 8A to the position shown in FIG. 9A. As the insertion fork moves distally, the joining member 74 pivots at both ends so that the distal end 92 of the joining member and the proximal end 96 of the insertion fork 75 pass through the central opening 137 of the top cap part 100 (FIGS. 6A-6C). In the extended position shown in FIG. 9A, the proximal section 72 of the firing rod extends along the axis $A_1$, the distal section 76 of the firing rod extends along the axis $A_2$ that defines an angle of about 25-35 degrees with the axis $A_1$, and the joining member 74 of the firing rod extends along the axis $A_3$ that is nonparallel to both $A_1$ and $A_2$.

Figure 10A:
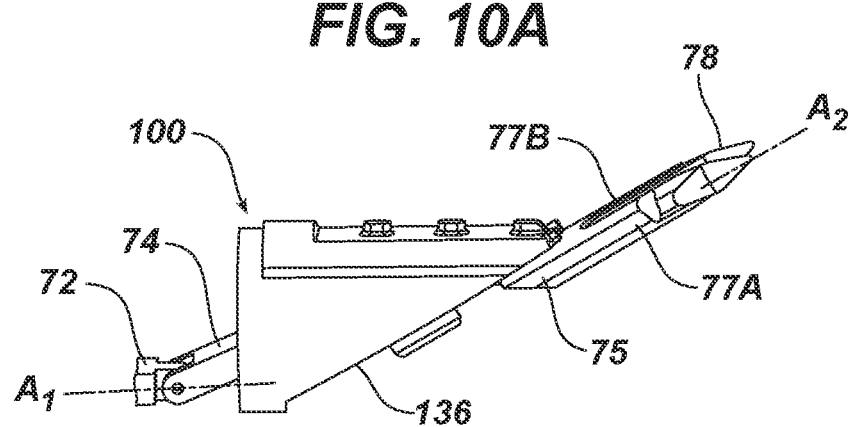
FIG. 10A shows the top cap part, the firing rod and the surgical fastener of FIG. 2.
Figure 10B:
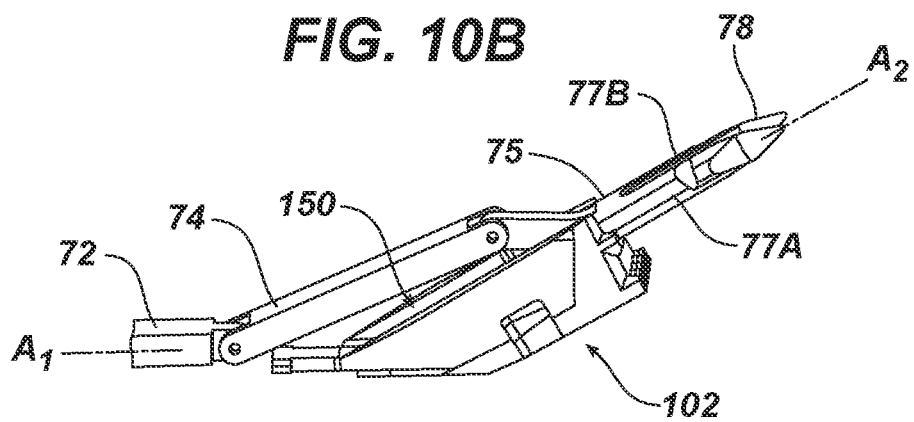
FIG. 10B shows the bottom cap part, the firing rod and the surgical fastener of FIG. 2.

Referring to FIGS. 10A and 10B, as the extension 72 of the proximal section of the firing rod moves distally along the axis $A_1$, the pivot connections at both ends of the joining member 74 enable the joining member to move away from the sloping floor 150 of the bottom cap part 102 and into the central space 137 (FIGS. 6A and 6B) of the top cap part 100. As the insertion fork 75 moves distally, the top surfaces of the tines 77A, 77B of the insertion fork 75 engage the sloping bottom surface 136 of the top cap part 100 for maintaining the orientation of tines 77A, 77B along the axis $A_2$. At the same time, the bottom surfaces of the tines 77A, 77B of the insertion fork 75 engage the sloping floor 150 of the bottom cap part 102 for maintaining the orientation of the tines 77A, 77B along the axis $A_2$. As a result, the surgical fastener 78 that is dispensed from the distal end cap 68 has a length that extends along the axis $A_2$. As a result, the surgical fastener is dispensed at an angle of about 25-35 degrees relative to the longitudinal axis $A_1$ of the elongated shaft.

In one embodiment, the applicator instrument 50 (FIG. 1) is a multi-fire device that contains a plurality of surgical fasteners pre-loaded therein as disclosed in commonly assigned U.S. Pat. Nos. 8,579,920; 8,728,098; 8,728,099; 8,894,669; and 8,920,439, the disclosures of which are hereby incorporated by reference herein. In one embodiment, the applicator instrument includes a plurality of surgical fasteners stored in series along the length of the elongated shaft. In one embodiment, the elongated shaft includes a pair of flat stampings having tabbed features incorporated therein. One of the flat stampings is a stationary, anti-backup stamping for preventing the surgical fasteners from moving proximally within the elongated shaft. The other flat stamping is an advancer stamping that cycles in distal and proximal directions each time the trigger is squeezed and released to facilitate incremental advancement of the surgical fasteners along the length of the elongated shaft. In one embodiment, the lead surgical fastener is staged for firing via a staging assembly having a spring. After the lead surgical fastener has been staged by the staging assembly, a firing rod pilots into the lead surgical fastener and delivers it through the surgical fastener dispensing window. In one embodiment, the elongated shaft is curved and the stampings are flexible so that the stampings may curve to conform to the curve of the shaft while guiding the surgical fasteners along the curved path defined by the shaft. In one embodiment, a single, lead surgical fastener is dispensed each time the trigger is pulled. During each trigger pull, each of the trailing surgical fasteners are advanced distally toward the distal end of the articulating shaft. In one embodiment, an applicator instrument is a single shot device that dispenses only one surgical fastener.

Figure 11:
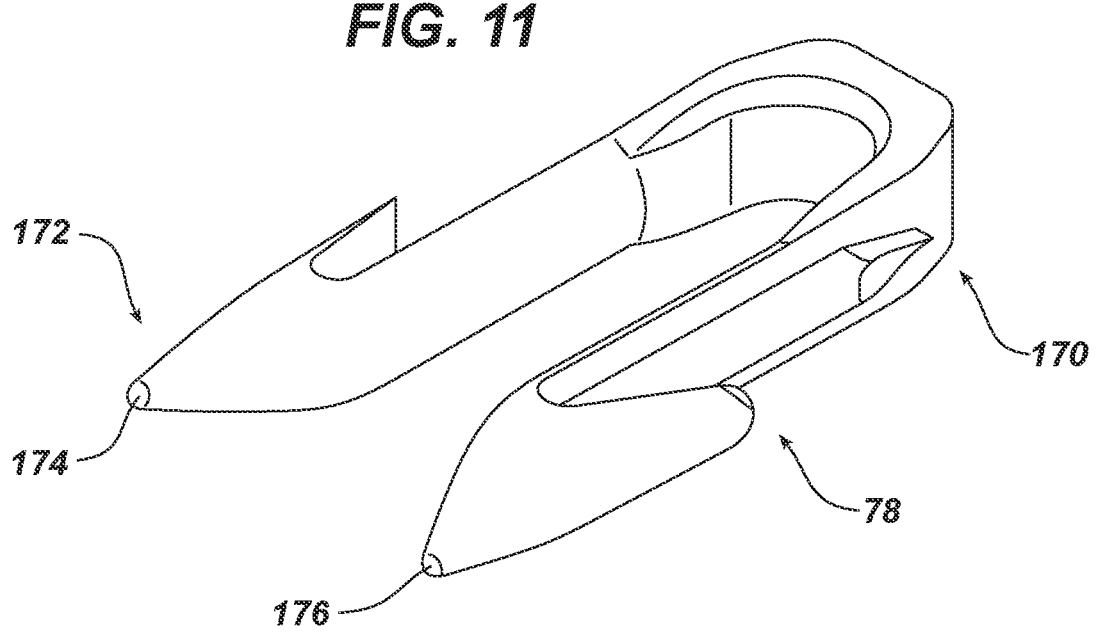
FIG. 11 shows a perspective view of the surgical fastener shown in FIG. 2.

In one embodiment, a series of surgical fasteners are pre-loaded into the elongated shaft 62 of the applicator instrument 50 (FIG. 1). Referring to FIG. 11, in one embodiment, a single surgical fastener 78 includes a proximal end 170 and a distal end 172 having insertion tips 174, 176 that are spaced from one another for capturing mesh fibers between the tapered ends. In one embodiment, the surgical fastener 78 has one or more of the features disclosed in commonly assigned U.S. Pat. Nos. 8,579,920; 8,728,098; 8,728,099; 8,894,669; and 8,920,439, the disclosures of which are hereby incorporated by reference herein.

Figure 12A:
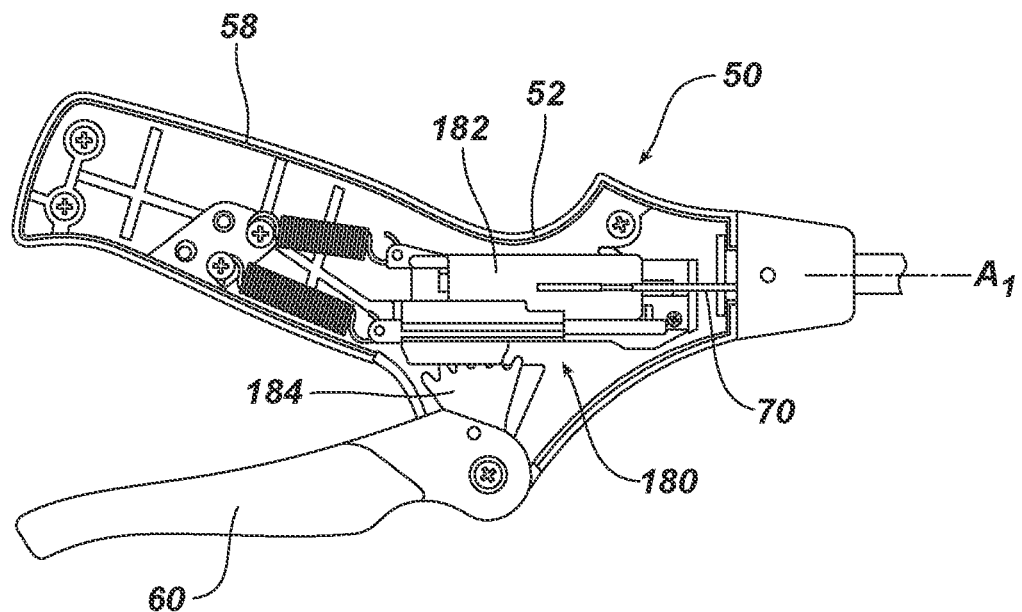
FIGS. 12A-12C show the applicator instrument of FIG. 1 during a firing cycle.
Figures 1, 12A:
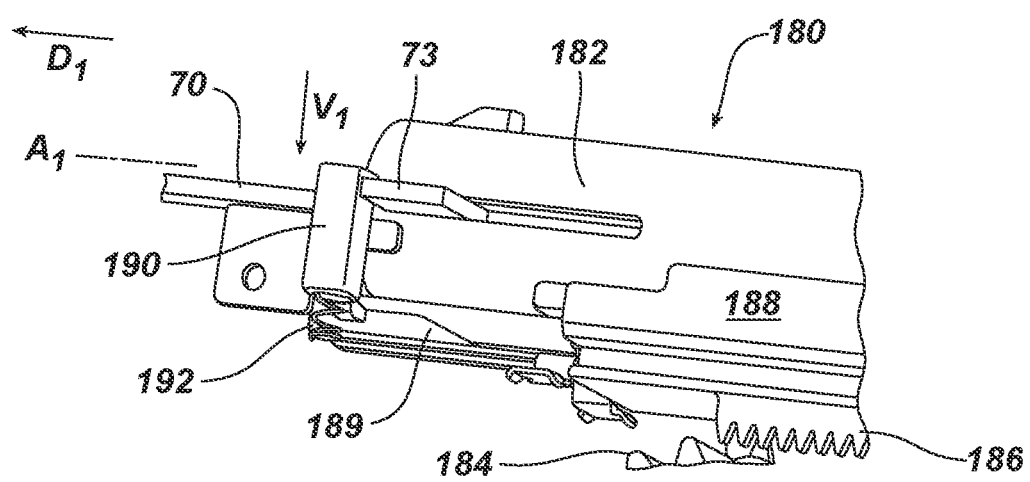

Referring to FIG. 12A, in one embodiment, the applicator instrument 50 includes the housing 52 that contains the firing system, and the handle 58 projecting upwardly and proximally from the housing. The applicator instrument includes the trigger 60 that is squeezed toward the handle 58 for activating a firing system 180. In one embodiment, the firing system 180 has one or more features similar to those disclosed in commonly assigned U.S. Pat. Nos. 8,579,920; 8,728,098; 8,728,099; 8,894,669; and 8,920,439, the disclosures of which are hereby incorporated by reference herein. In one embodiment, the firing system 180 includes a spring block 182, the firing rod 70, and a firing spring (not show) located inside the spring block 182 that stores energy as the trigger 60 is squeezed. In one embodiment, the firing system 180 is coupled with the trigger 60 via a trigger gear 184 that rotates in a clockwise direction as the trigger 60 is squeezed. The trigger gear 184 is coupled with teeth 186 on a sliding yoke 188. As the trigger gear 184 rotates in a clockwise direction, the yoke 188 slides in a distal direction along the axis $A_1$-$A_1$. As the trigger gear 184 rotates in a counter-clockwise direction, the yoke 188 slides in a proximal direction along the axis $A_1$-$A_1$.

Referring to FIG. 12A-1, in one embodiment, the firing system 180 includes a firing rod release 190 and a release spring 192 that normally holds the firing rod release 190 in the upright position, which is shown in FIG. 12A-1. When the firing rod release 190 is in the upright position, it engages a lateral extension 73 of the firing rod 70 for restraining distal movement $D_1$ (i.e., to the left in FIG. 12A-1) of the firing rod 70 along the longitudinal axis $A_1$. The distal end of the yoke 188 has a sloping surface 189 that is adapted to engage the lower end of the firing rod release 190 for moving the firing rod release down in the direction designated $V_1$.

Figure 12B:
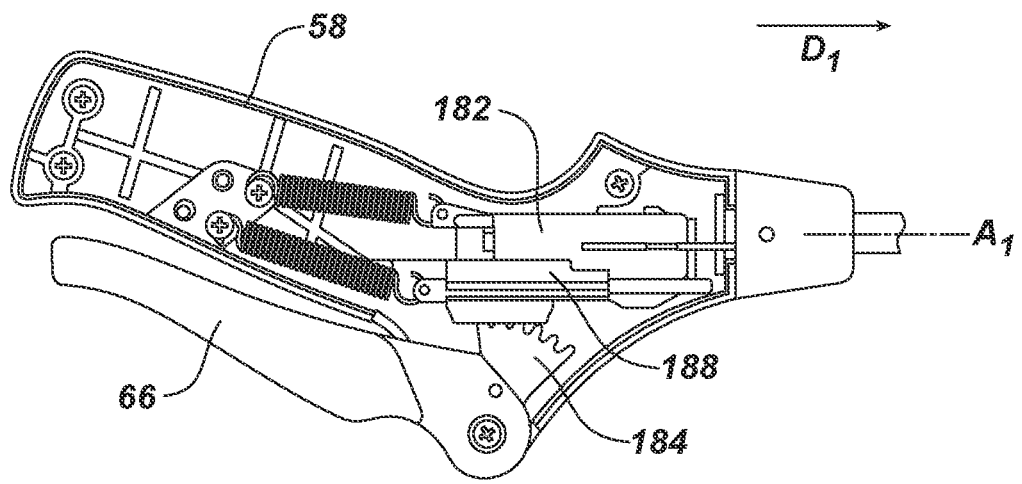
Figures 1, 12B:
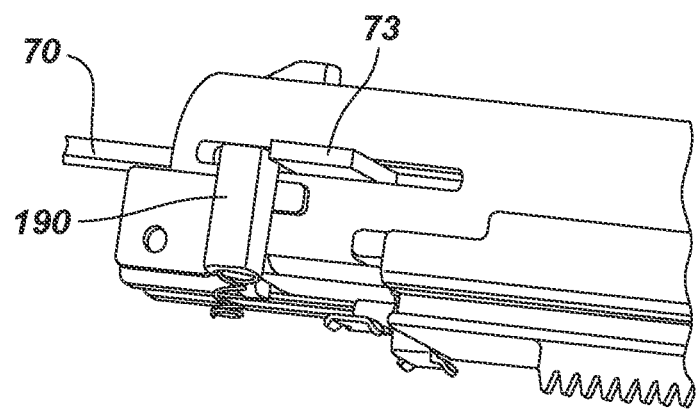

Referring to FIGS. 12A and 12B, as the trigger 60 is squeezed toward the handle 58, the trigger gear 184 urges the yoke 188 and the spring block 182 in a distal direction $D_1$ along the longitudinal axis $A_1$. At the same time, the upper end of the firing rod release 190 engages the lateral extension 73 of the firing rod 70 for restraining the firing rod 70 from moving distally. As the trigger is squeezed, energy is stored in the firing rod spring (not shown) located inside the spring block 182.

Figure 12C:
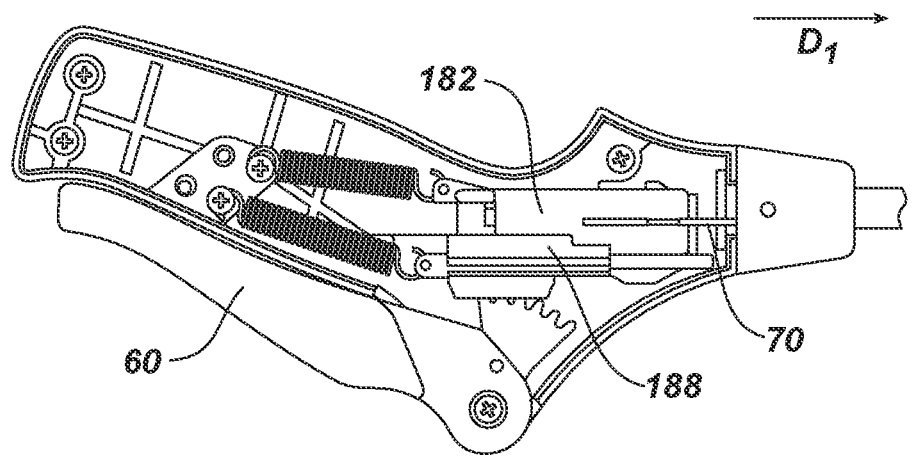
Figures 1, 12C:
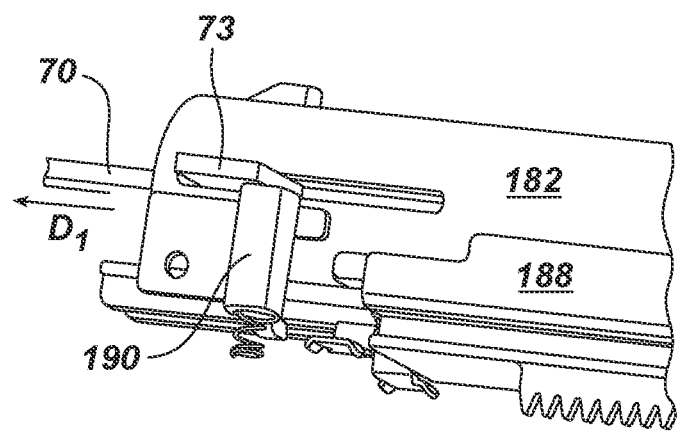
Figure 13:
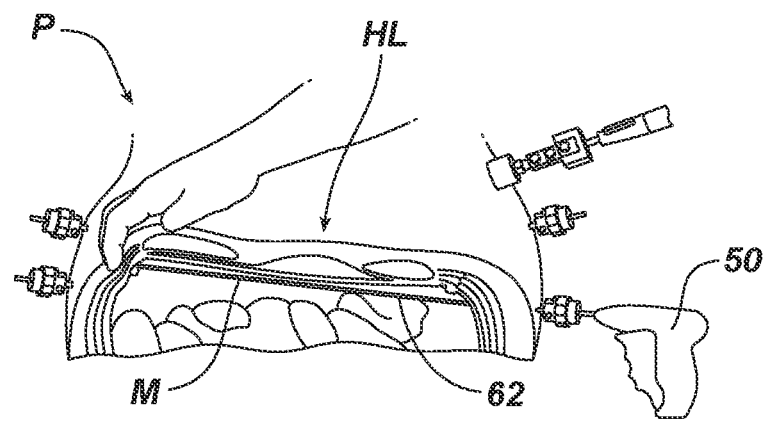
FIG. 13 shows a hernia repair procedure using an applicator instrument for dispensing surgical fasteners, in accordance with one embodiment of the present invention.

Referring to FIGS. 12C and 12C-1, the trigger 60 is squeezed further for storing additional energy in the firing rod spring located inside the spring block 182. The sloping surface 189 (FIG. 12A-1) of the yoke 188 forces the firing rod release 190 to the position shown in FIG. 12C-1 whereupon the lateral extension 73 of the firing rod 70 is free to move in the distal direction $D_1$, which may be along the axis $A_1$ (FIG. 12B). The energy stored in the firing rod spring is transferred to the firing rod 70 for driving the firing rod 70 in the distal direction $D_1$ for dispensing a surgical fastener from the distal end of the applicator instrument.

Figure 14:
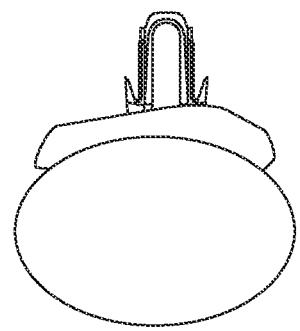
FIG. 14 shows a surgical procedure for attaching Cooper's ligament to a public bone.

Referring to FIG. 14, in one embodiment, a patient P with a hernia defect is prepared for a laparoscopic hernia repair procedure. The patient P is examined and the hernia location HL is identified using palpation or other methods. The patient is administered conventional general anesthesia in a conventional manner by induction and inhalation. A Veress needle is inserted into the abdominal cavity through the skin. A pneumoperitoneum of 8-15 mmHg is created. One 10 mm trocar is inserted in the left upper quadrant of the abdomen as far lateral as possible. A 30 degree laparoscopic camera is inserted through the trocar and the contents of the abdominal cavity are assessed. Two additional 5 mm trocars are placed laterally on the same side as the 10 mm port. Laparoscopic instruments are used to reduce the contents of hernia. The edges of the healthy fascia around the defect are examined and any attachments of viscera to the abdominal wall are divided to create a free space for fixation of the mesh. The size of the defect is assessed. In one embodiment, the defect may be primarily closed with sutures, if desired.

At this point in the procedure, the surgeon then prepares a mesh hernia patch. The mesh M is sized to ensure adequate overlap beyond the margins of the defect on all sides. The mesh is rolled and inserted into the abdominal cavity through the 10 mm trocar. The mesh is unrolled and placed over the defect. Stay sutures may be placed through the mesh into the abdominal tissue as desired, i.e. at the four compass points of the mesh (North, South, East, West).

In one embodiment, an applicator instrument 50 as disclosed herein is inserted through one of the 5 mm trocars. The distal end cap 68 on the elongated shaft 62 of the applicator instrument 50 may be used to manipulate the mesh M and place the mesh in a desired location prior to being fixated. In one embodiment, the trigger 60 of the applicator instrument 50 is deployed (e.g., squeezed) to deliver surgical fasteners through the mesh M and into the abdominal wall. The perimeter of the mesh M is fixated using a plurality of surgical fasteners in a crown configuration. In one embodiment, a second inner crown of surgical fasteners may also be applied, if desired. In one embodiment, the surgeon may move the applicator instrument to one of the other trocars, if desired.

The mesh repair is inspected to ensure it is sufficiently fixated to the abdominal wall. The applicator instrument is removed from the trocar. The camera, laparoscopic instruments, and trocars are removed from the abdominal cavity. The trocar incisions may be closed using appropriate suturing or closure techniques. The patient is moved to a recovery room.

Referring to FIG. 14, in one embodiment, during laparoscopic inguinal hernia repairs, it is often desirable to deliver a fixation point directly over Cooper's ligament. However, directly beneath the ligament is the rigid pubic bone. Because the Cooper's ligament is very thin (e.g., 1-3 mm), it is difficult to deliver fasteners 78 (which may have a length of about 6-8 mm) directly onto the Cooper's ligament. However, if surgical fasteners could be delivered at an angle relative to the tissue the surgical fasteners will scythe across the pubic bone and secure more effectively. One or more of the applicator instruments disclosed herein may be used to provide for this angled delivery.

Figure 15:
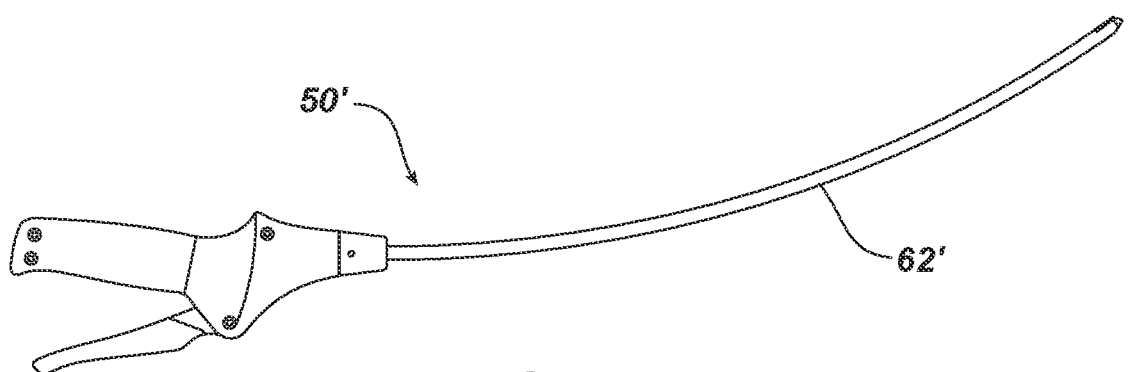
FIG. 15 shows a side elevation view of an applicator instrument for dispensing surgical fasteners including a housing, an actuator, an elongated, curved shaft, and a distal end cap, in accordance with one embodiment of the present invention.

Referring to FIG. 15, in one embodiment an applicator instrument 50' for dispensing surgical fasteners has a curved shaft 62'. In one embodiment, the firing rod and the stampings are flexible so that the firing rod and the stampings may curve to conform to the curve of the shaft 62' while guiding the surgical fasteners along the curved path of the elongated shaft. The applicator instrument is configured to dispense off-axis surgical fasteners as disclosed herein.

Referring to FIG. 16, in one embodiment, an applicator instrument 250 includes an elongated shaft 262 and a firing rod 270 that reciprocates in distal and proximal directions along a longitudinal axis $A_1$. The distal end of the firing rod includes a flexible insertion fork 275. The flexible insertion fork 275 has tines 277A, 277B that engage the legs of a surgical fastener 278. The applicator instrument includes a distal end cap 268 having a curved ramp formed therein. As will be described in more detail herein, the curved ramp changes the orientation of the surgical fastener 278 so that it is dispensed at an angle relative to the longitudinal axis $A_1$ of the elongated shaft 262. The flexible insertion fork 275 is adapted to curve as it passes through the curved ramp section of the distal end cap 268.

Referring to FIGS. 17A and 17B, in one embodiment, the tines 277A, 277B of the flexible insertion fork 275 engage the legs of the surgical fastener 278. When in an advanced position, the flexible insertion fork 275 extends beyond a distal-most end of the distal end cap 268 for dispensing the surgical fastener 278. FIG. 17B shows the flexible insertion fork 275 in a straight configuration, however, the flexible insertion fork is adapted to curve for passing through a curved ramp located within the distal end cap 268. In one embodiment, the distal end cap 268 can be toggled between a curved path and a straight path for the flexible insertion fork 275.

Referring to FIG. 18, in one embodiment, a distal end cap 268 is secured to a distal end of an elongated shaft 262 of an applicator instrument 250. The distal end cap 268 includes a curved ramp 279 disposed therein that guides the distal movement of the flexible insertion fork 275. In one embodiment, a plurality of surgical fasteners 278A, 278B are pre-loaded inside the elongated shaft 262. Although only two surgical fasteners are shown, up to twenty, thirty, or more surgical fasteners may be pre-loaded into the elongated shaft 262. In one embodiment, each time a trigger on the applicator instrument is squeezed, an advancer (not shown) moves distally for advancing the surgical fasteners one position closer to the distal end of the elongated shaft 262. A lead surgical fastener 278A (i.e., the distal-most surgical fastener) is engaged by the flexible insertion fork 275 at the distal end of the shaft. As the flexible insertion fork 275 drives the lead surgical fastener 278A through the distal end cap 268, the flexible insertion fork 275 curves to follow the curved path of the curved ramp 279. As the lead surgical fastener 278A is dispensed from the distal end cap 268, it is dispensed along an axis $A_2$ that defines an angle of about 25-35 degrees (designated a1) relative to the longitudinal axis $A_1$ of the elongated shaft 262.

Referring to FIG. 19A, in one embodiment, an applicator instrument 350 includes an elongated shaft 362 and a distal end cap 368 secured to the distal end of the elongated shaft. The applicator instrument has a firing system including a firing rod 370 having a flexible insertion fork 375, an advancer 390 that advances surgical fasteners 378 toward the distal end of the elongated shaft, an anti-backup stamping 392 that prevents the surgical fastener 378 from moving proximally, and a staging assembly 394 that shifts the lead surgical fastener 378A from a first position in which it is aligned with the advancer 390 to a second position in which it is aligned with the flexible insertion fork 375. The distal end cap 368 has a curved ramp 379 disposed therein that is designed to change the orientation of a surgical fastener as it passes through the distal end cap 368.

Referring to FIG. 19B, in one embodiment, as the trigger is pulled, energy is stored in the firing rod spring and the advancer 390 advances the surgical fasteners distally so that the lead surgical fastener 278A is loaded onto the staging assembly 394. Referring to FIG. 19C, as the trigger is pulled further, the advancer 390 retracts so that the staging assembly 394 is free to shift the lead surgical fastener 378A into alignment with the flexible insertion fork 375.

Referring to FIG. 19D, in one embodiment, the trigger is further pulled for moving the flexible insertion fork 375 in a distal direction for piloting the tines of the flexible insertion fork onto the legs of the lead surgical fastener 378A. Referring to FIG. 19E, in one embodiment, the firing rod release (not shown) disengages from the proximal lateral extension of the firing rod 370. The energy stored in the firing rod spring drives the firing rod 370 and the flexible insertion fork 375 in a distal direction. The flexible insertion fork 375 curves as it passes through the curved ramp 379 of the distal end cap 368. As the lead surgical fastener 378A is dispensed from the distal end cap 368, it extends along an axis $A_2$ that defines an angle of about 30 degrees with the longitudinal axis $A_1$ of the elongated shaft 362. Referring to FIGS. 19E-1 and 19E-2, the curved ramp inside the distal end cap 368 curves the flexible insertion fork 375 so that the lead surgical fastener 378A extends along an axis $A_2$ that defines an angle of about 30 degrees with the longitudinal axis $A_1$ of the elongated shaft 362.

Figure 20:
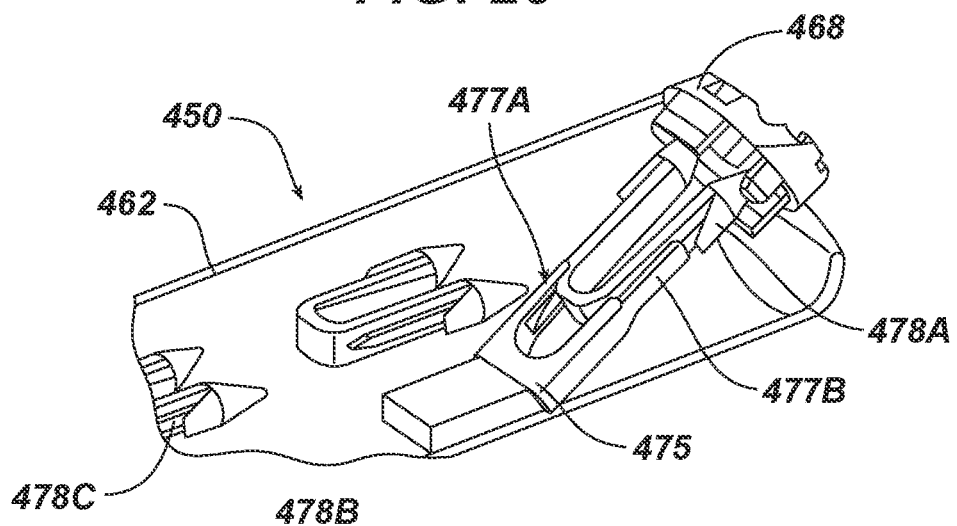
FIG. 20 shows an applicator instrument having a firing rod with a distal section including an insertion fork, in accordance with one embodiment of the present invention.

Referring to FIG. 20, in one embodiment, an applicator instrument 450 has an elongated shaft 462 with a distal end cap 468 secured to the distal end of the elongated shaft. The applicator instrument includes a firing rod having a distal section including an insertion fork 475 having tines 477A, 477B that engage the legs of a surgical fastener 478A for dispensing the surgical fastener from the distal end of the elongated shaft. Although not shown in FIG. 20, in one embodiment, the proximal end of the insertion fork 475 is connected with a proximal section of a firing rod of a firing system as shown and described herein.

In one embodiment, a plurality of surgical fasteners are disposed inside the elongated shaft 462 of the applicator instrument 450. In one embodiment, each time the trigger of the applicator instrument is pulled, the series of surgical fasteners are shifted distally toward the distal end of the elongated shaft. In one embodiment, the surgical fasteners may be urged distally by a spring in contact with one or more of the surgical fasteners. In one embodiment, the surgical fasteners 478 move distally through the elongated shaft at a first elevation. Upon reaching a distal-most position, the lead surgical fastener 478A is dropped down to a second elevation in alignment with the tines 477A, 477B of the insertion fork 475.

Figure 21:
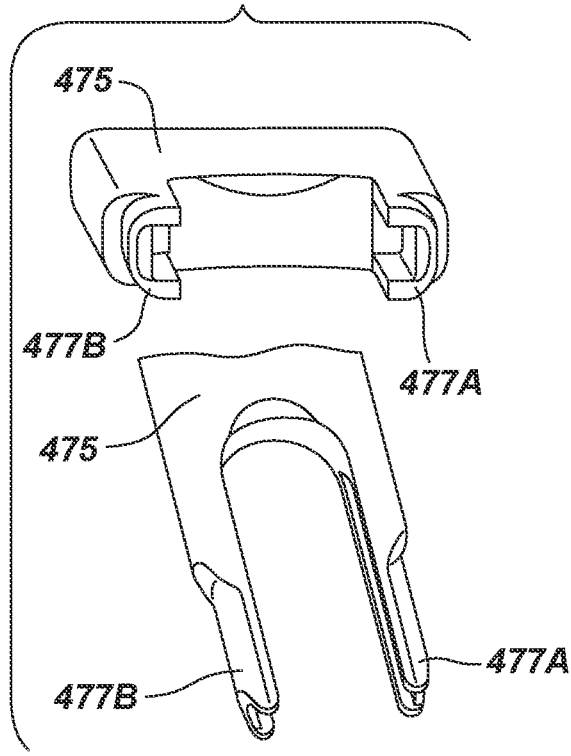
FIG. 21 shows an insertion fork for an applicator instrument, in accordance with one embodiment of the present invention.

Referring to FIG. 21, in one embodiment, the tines 478A, 478B of the insertion fork 475 have a C-shaped cross section that extends along the length of the respective tines. This requires the proximal end of the lead surgical fastener 478A (FIG. 20) to completely clear the distal-most ends of the tines 477A, 477B so that the tines may receive the legs of the lead surgical fastener 478A.

Figure 22:
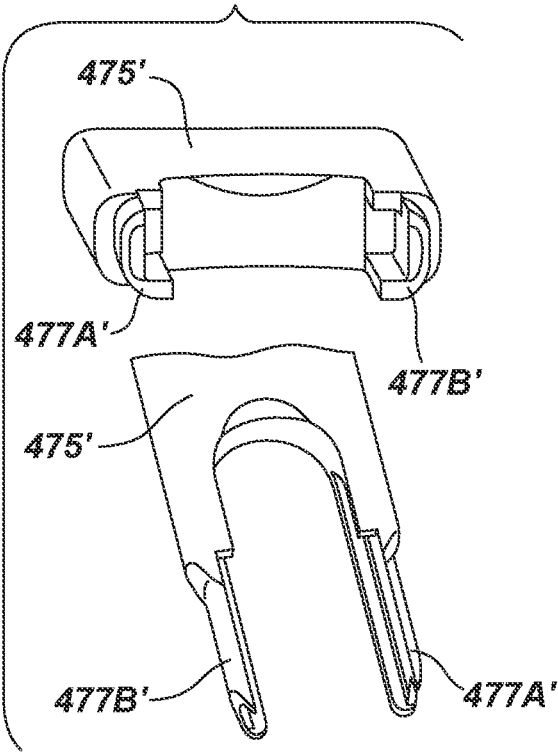
FIG. 22 shows an insertion fork for an applicator instrument, in accordance with another embodiment of the present invention.

Referring to FIG. 22, in order to reduce the amount of clearance space required to load the lead surgical fastener 478A (FIG. 20) onto the tines 477A', 477B' of an insertion fork 475', in one embodiment, the tines have a C-shaped cross-section adjacent the proximal ends of the tines and an L-shaped cross-section adjacent the distal ends of the tines and. The L-shaped cross-section facilitates loading the lead surgical fastener onto the tines from above by reducing the amount of clearance space that is required between the proximal end of the surgical fastener and the distal receiving ends of the tines 477A', 4776'.

Figure 23:
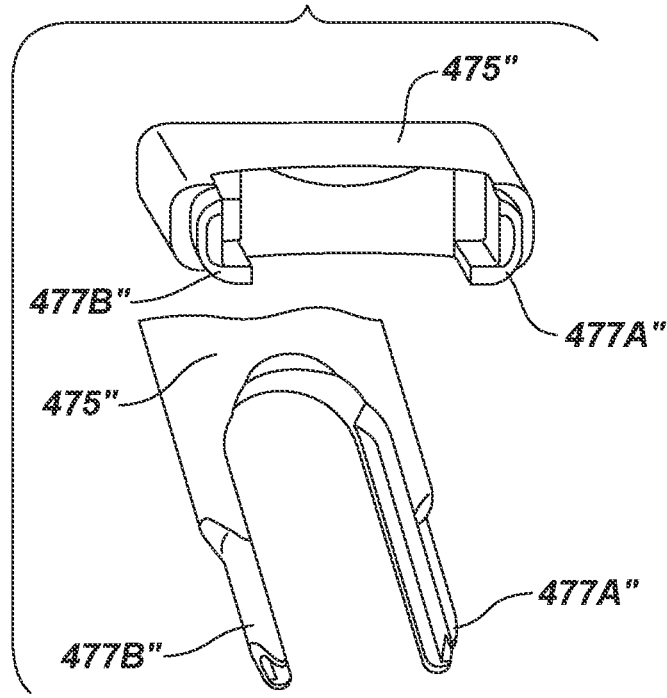
FIG. 23 shows an insertion fork for an applicator instrument, in accordance with yet another embodiment of the present invention.

Referring to FIG. 23, in order to further reduce the amount of clearance space required to load the lead surgical fastener 478A (FIG. 20) onto the tines 477A", 477B''' of an insertion fork 475", in one embodiment, the tines have an L-shaped cross-section that extends along the entire length of the respective tines. The L-shaped cross-section facilitates loading the lead surgical fastener onto the tines from above by further reducing the amount of clearance space that is required between the proximal end of the surgical fastener and the distal receiving ends of the tines 477A", 477B". The insertion fork 475" of FIG. 23 requires less clearance space than the insertion fork 475' of FIG. 22, which, in turn, requires less clearance space than the insertion fork 475 of FIG. 21.

Figure 24:
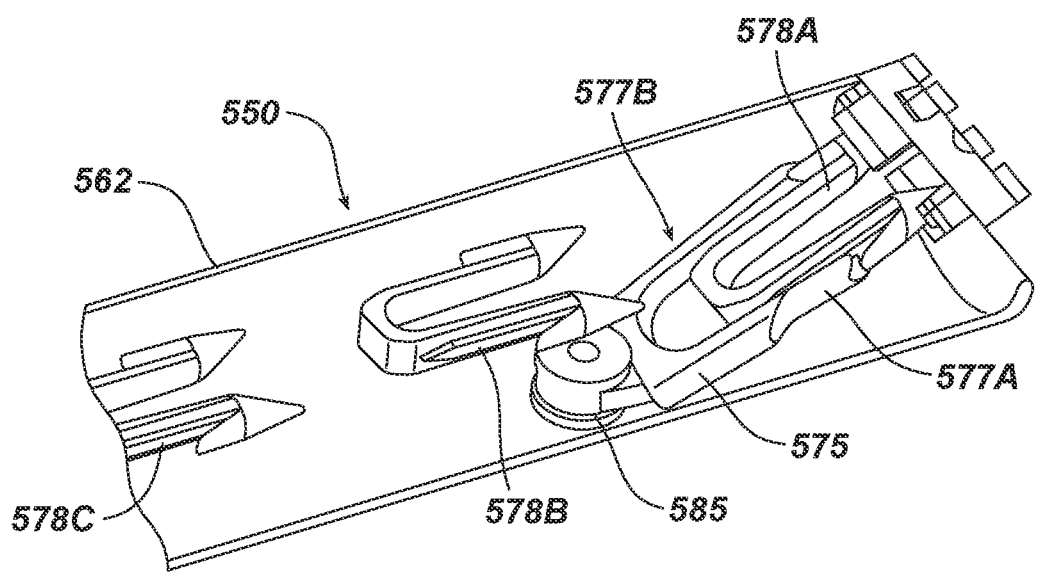
FIG. 24 shows an applicator instrument having a firing rod with a distal section including an insertion fork with tines that can be opened, in accordance with still another embodiment of the present invention.

Referring to FIG. 24, in one embodiment, the tines of an insertion fork move between an open position for loading a surgical fastener onto the insertion fork and a closed position for securing the surgical fastener between the tines of the insertion fork. In one embodiment, the tines are further apart when the insertion fork is in the open position and closer together when the insertion fork is in the closed position. In one embodiment, a spring assembly may normally hold the tines in the open configuration for loading a surgical fastener onto the insertion fork. In one embodiment, an applicator instrument 550 has an elongated shaft 562 with a distal end cap 568 secured to the distal end of the elongated shaft. The applicator instrument includes an insertion fork 575 having tines 577A, 577B that engage the legs of a surgical fastener 578A for dispensing the surgical fastener from the distal end of the elongated shaft. In one embodiment, the insertion fork 575 includes a spring assembly 585 that is coupled with the tines 577A, 577B of the insertion fork. The spring assembly 585 normally maintains the tines 577A, 577B in an open configuration in which the legs of the lead surgical fastener 578A may drop down to a position between the open tines of the insertion fork for loading a lead surgical fastener onto the tines. In one embodiment, after the lead surgical fastener is aligned between the tines, the tines are moved into a closed configuration for firmly securing the surgical fastener between the tines of the insertion fork. In one embodiment, the firing system may have a cam surface that engages the insertion fork for moving the tines into the closed configuration. Although not shown in FIG. 24, in one embodiment, a proximal end of the insertion fork 575 is coupled with a firing rod that dispenses surgical fasteners from the distal end of the elongated shaft 562, as shown and described herein. In one embodiment, the spring assembly may normally maintain the tines in a closed position, and the tines open during an early stage of a firing cycle for loading a surgical fastener onto the insertion fork 576. The tines would then be closed for firing.

Figure 25A:
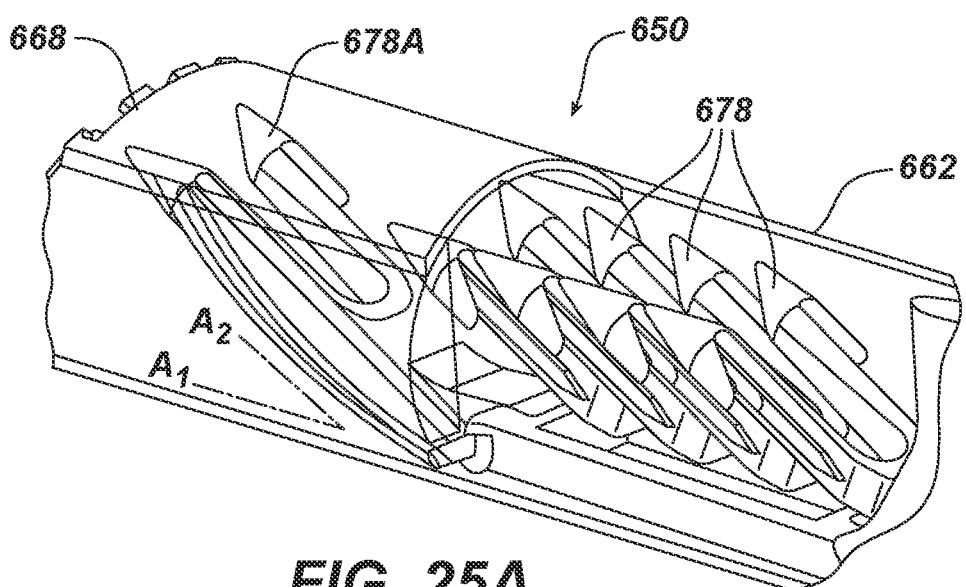
FIG. 25A shows an applicator instrument for dispensing surgical fasteners including an elongated shaft, surgical fasteners pre-loaded into the elongated shaft, a firing rod, and a distal end cap, in accordance with one embodiment of the present invention.
Figure 25B:
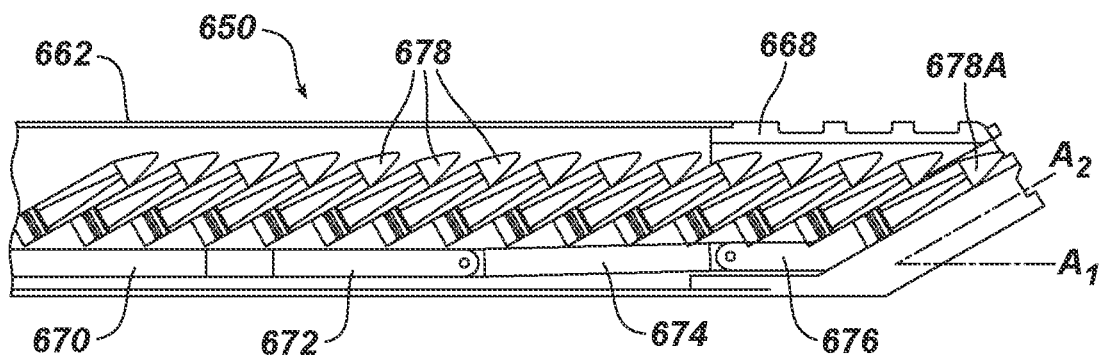
FIG. 25B shows a cross-sectional view of the applicator instrument shown in FIG. 25A.

Referring to FIGS. 25A and 25B, in one embodiment, an applicator instrument 650 includes an elongated shaft 662 and a distal end cap 668 secured to the distal end of the elongated shaft. A plurality of surgical fasteners 678 are pre-loaded into the elongated shaft. In one embodiment, the surgical fasteners 678 are stacked at an angle relative to the longitudinal axis $A_1$ of the elongated shaft. In one embodiment, the surgical fasteners 678 have respective lengths that extend along an axis $A_2$ that define an angle of about 30 degrees with the longitudinal axis $A_1$ of the elongated shaft 662. In one embodiment, the applicator instrument 650 has a firing system including a firing rod having a proximal section 670, an extension 672, a joining member 674 having a proximal end pivotally connected to the distal end of the extension 672, and a distal end 676 including an insertion fork having a proximal end pivotally connected with the distal end of the joining member 674. In one embodiment, during a firing cycle, a lead surgical fastener 678A is loaded onto the insertion fork for being dispensed from the distal end cap 668, whereby the lead surgical fastener 678A is dispensed at an angle relative to the longitudinal axis of the elongated shaft 662. In one embodiment, the fastener dispensing angle is along the same axis $A_2$ along which the fasteners are stored.

Figure 26:
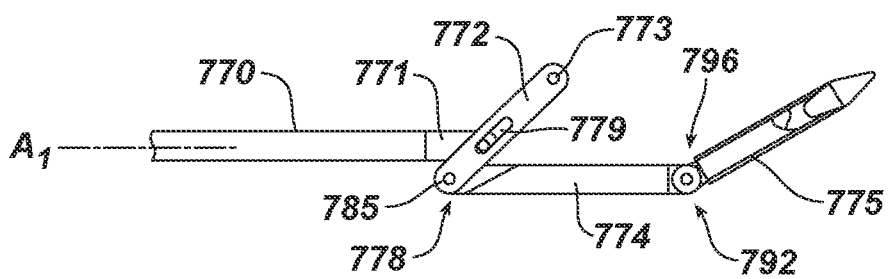
FIG. 26 shows a firing rod for an applicator instrument for dispensing surgical fasteners, in accordance with one embodiment of the present invention.

In one embodiment, an applicator instrument for dispensing surgical fasteners includes one or more elements that extend outside the elongated shaft of the applicator instrument. Referring to FIG. 26, in one embodiment, a firing system includes a firing rod having a proximal section 770 and an extension 771 that are adapted to move distally and proximally along a longitudinal axis $A_1$ during a firing cycle. The extension is pivotally connected with a pivoting member 772. In one embodiment, the pivoting member 772 has an upper end with a first pivot point 773, a lower end with a second pivot point 785, and an elongated slot 779 located between the first and second pivot points 773, 785. In one embodiment, the distal end of the extension 771 is pivotally and slidably secured to the pivoting member 772 at the elongated slot 779. In one embodiment, the first pivot point 773 is fixed inside of an elongated shaft 762. In one embodiment, the second pivot point 785 of the pivoting member 772 is pivotally connected with the proximal end 778 of a joining member 774, and the distal end 792 of the joining member 774 is pivotally connected with the proximal end 796 of the insertion fork 775.

Figure 27A:
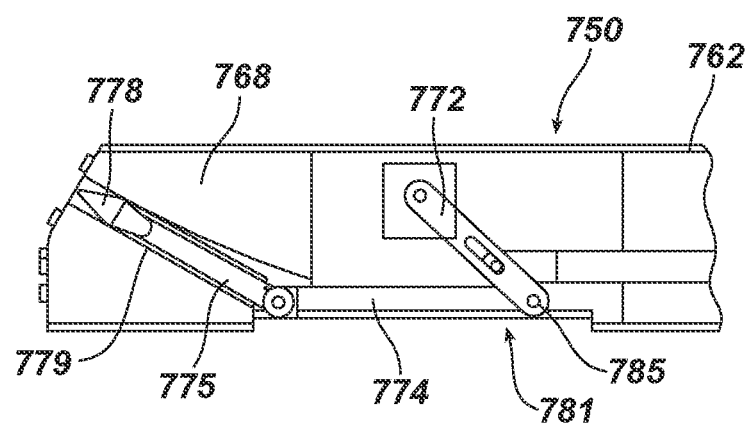
FIGS. 27A-27C show an applicator instrument including the firing rod shown in FIG. 26.

Referring to FIG. 27A, in one embodiment, an applicator instrument 750 includes the elements of FIG. 26 assembled inside an elongated shaft 762. The applicator instrument 750 includes a distal end cap 768 secured to the distal end of the elongated shaft 762. The distal end cap 768 has an angled ramp 779 provided therein that controls the orientation of the insertion fork 775 and the surgical fastener 778 as the surgical fastener is dispensed from the distal end cap 768. In one embodiment, the first pivot point 773 of the pivoting member 772 is pivotally connected with the elongated shaft 762. The outer wall of the elongated shaft 762 has an opening 781 formed therein that is aligned with the second pivot point 785 of the pivoting member 772. During a firing cycle, the opening 781 provides a space for the pivoting member 772 and the joining member 774 to travel outside the outer wall of the elongated shaft.

Referring to FIG. 27A, in one embodiment, during a first phase of a firing cycle, the lead surgical fastener 778 is loaded onto the insertion fork 775. The orientation of the insertion fork 775 and the surgical fastener 778 is controlled by the angled ramp 779. The pivoting member 772 and the joining member 774 are located inside the perimeter of the outer wall of the elongated outer shaft 762.

Figure 27B:
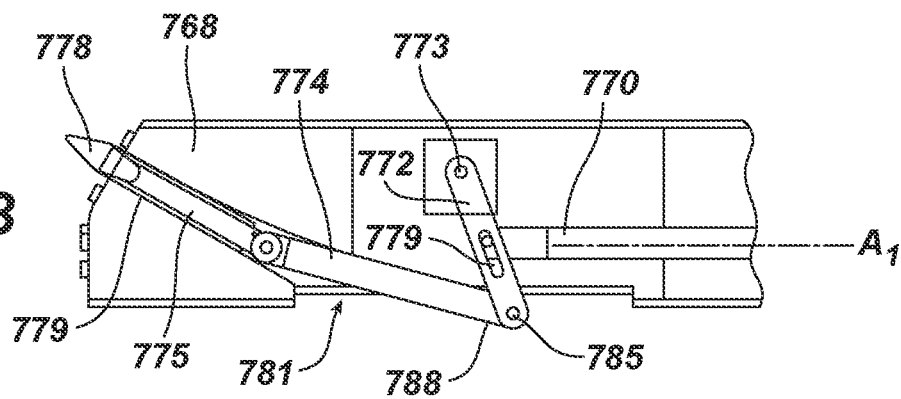

Referring to FIG. 27B, in one embodiment, during a second phase of the firing cycle, the firing rod 770 has moved distally along the longitudinal axis $A_1$. The extension 771 of the proximal section 770 of the firing rod, which is pivotally connected with the elongated slot 779 of the pivoting member 772, slides within the elongated slot 779, which, in turn, swings the second pivot point 785 in a distal direction about the first pivot point 773. The pivoting movement of the pivoting member 772 results in the second pivot point 785 and the proximal end 788 of the joining member 774 passing through the opening 781 and outside the elongated shaft 762. At the same time, the insertion fork 775 and the lead surgical fastener 778 moves distally along the angled ramp 779 for advancing the surgical fastener 778 beyond the distal end face of the distal end cap 768.

Figure 27C:
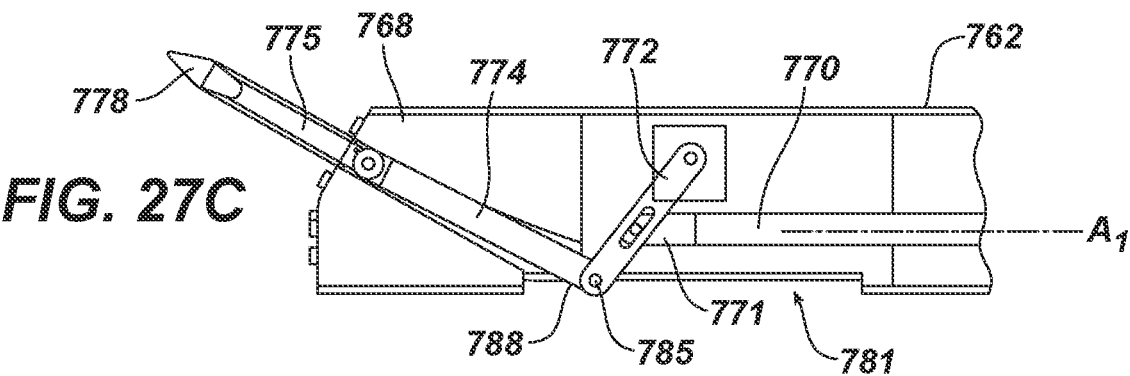
Figures 1, 27C:
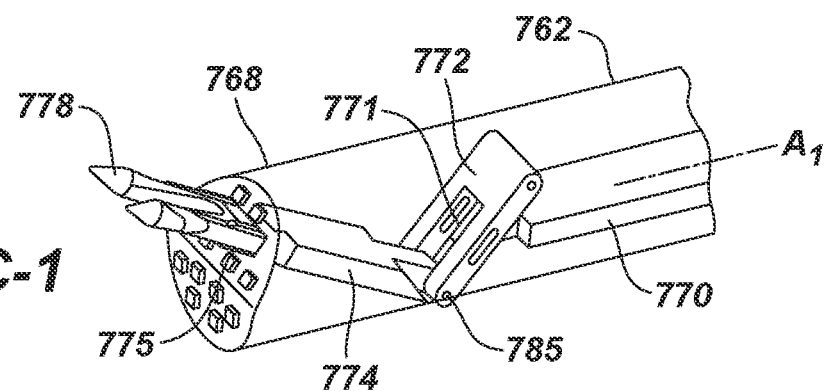

Referring to FIGS. 27C and 27C-1, during a third phase of the firing cycle, the proximal section 770 of the firing rod moves to its distal-most position along the longitudinal axis $A_1$. The extension 771 of the proximal section 770 slides further within the elongated slot 779 of the pivoting member 772, which, in turn, further swings the second pivot point 785 in a distal direction about the first pivot point 773. The pivoting movement of the pivoting member 772 results in the second pivot point 785 and the proximal end 788 of the joining member 774 passing distally through the opening 781 in the outside wall of the elongated shaft 762. During the third phase of the firing cycle, the insertion fork 775 continues to move distally along the angled ramp 779 for dispensing the surgical fastener 778 from the distal end cap 768.

Figure 28:
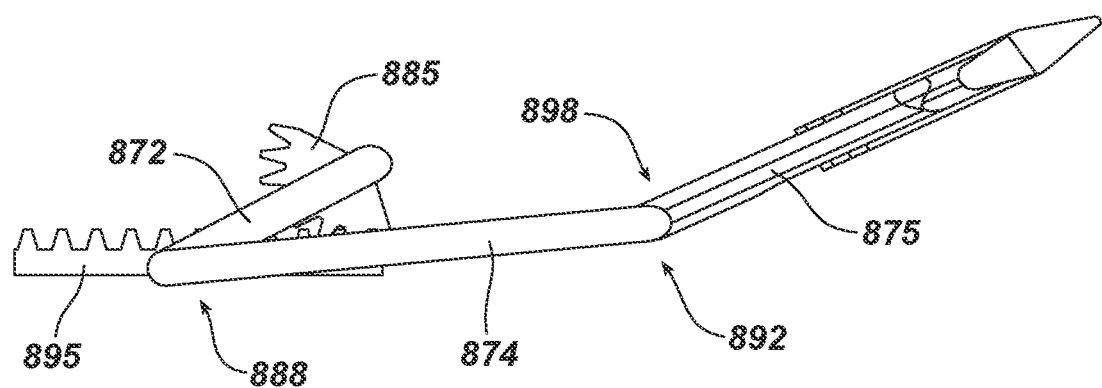
FIG. 28 shows a firing rod for an applicator instrument for dispensing a surgical fastener, in accordance with one embodiment of the present invention.

Referring to FIG. 28, in one embodiment, an applicator instrument includes a firing system having a rack and pinion arrangement for moving the insertion fork 875 in distal and proximal directions. In one embodiment, the firing system includes the rack 895, a pivoting member 872 having a pinion 885 that meshes with the rack 895, a joining member 874 having a proximal end 888 pivotally connected with the pivoting member 872, and an insertion fork 875 having a proximal end 898 pivotally connected with the distal end 892 of the joining member 874. In one embodiment, the pinion 885 is pivotally connected with the elongated shaft of the applicator instrument for swinging about a pivot point.

Figure 29:
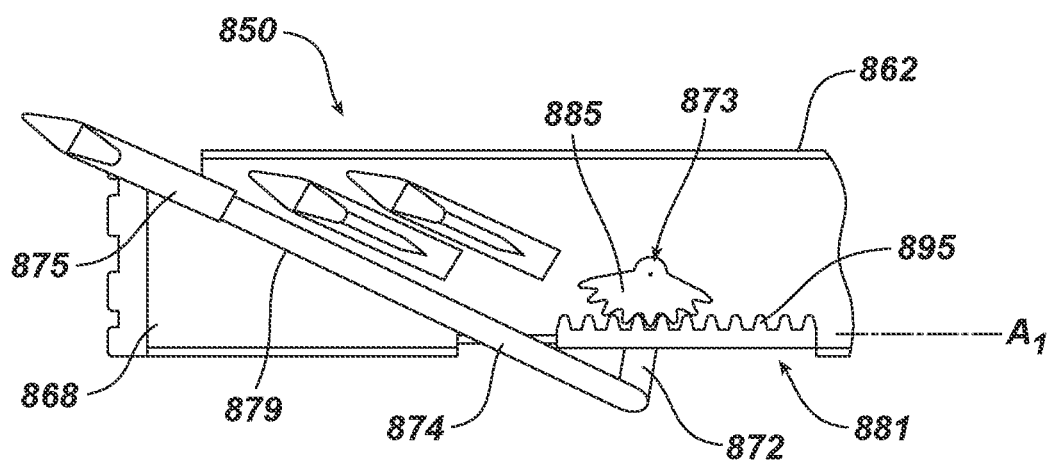
FIG. 29 shows an applicator instrument including the firing rod shown in FIG. 28.

Referring to FIG. 29, in one embodiment, an applicator instrument 850 includes an elongated shaft 862 with an opening 881 similar to that shown above in FIGS. 27A-27C, which allows the pivoting member 872 and the joining member 874 to pass through the opening 881 during a firing cycle. In one embodiment, the applicator instrument 850 includes a distal end cap 868 having an angled ramp 879 disposed therein for controlling the orientation angle of the insertion fork 875 as it moves distally and proximally. The rack 895 is secured to the distal end of the firing rod and moves distally and proximally along a longitudinal axis $A_1$. The pinion 885 is pivotally connected with the elongated shaft at pivot point 873. During a firing cycle, the rack 895 moves distally to rotate the pinion 885 in a clockwise direction (FIG. 29) about the pivot point 873. As a result, the pivot member 872 rotates in a clockwise direction with the pinion 885, which, in turn, advances the joining member 874 and the insertion fork 875 distally. The pivot member 872 and the joining member 874 pass through the opening 881 when moving from a first position shown in FIG. 28 to a second position shown in FIG. 29.

Figure 30A:
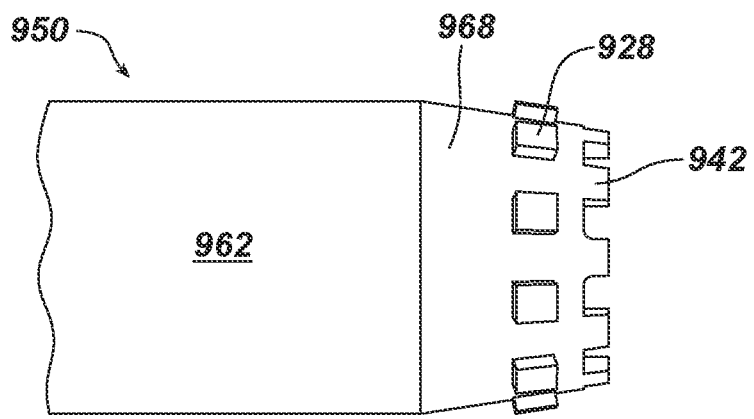
Figure 30B:
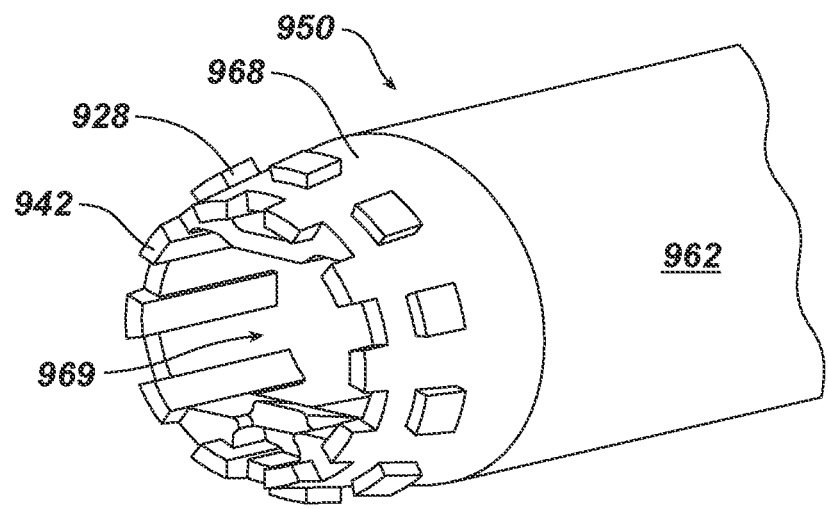
Figure 30C:
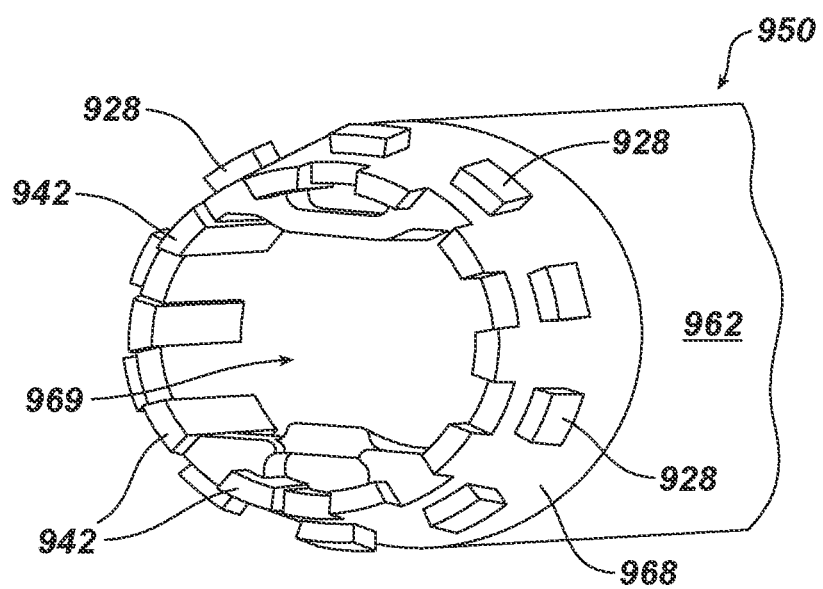

Referring to FIGS. 30A-30C, in one embodiment, an applicator instrument 950 includes an elongated shaft 962 having a distal end cap 968 secured to the distal end of the elongated shaft. The distal end cap 968 has a surgical fastener dispenser opening 969 formed in a distal end face. In one embodiment, the distal end cap 968 includes a first set of gripping elements 928 that extend radially outwardly from an outer wall of the distal end cap. In one embodiment, the first set of gripping elements 928 are evenly spaced from one another about the outer wall of the distal end cap 968. In one embodiment, the distal end cap includes a second set of gripping elements 942 that extend axially from the distal end face of the distal end cap. The second set of gripping elements 942 are evenly spaced from one another about the surgical fastener dispenser opening 962.

Figure 31A:
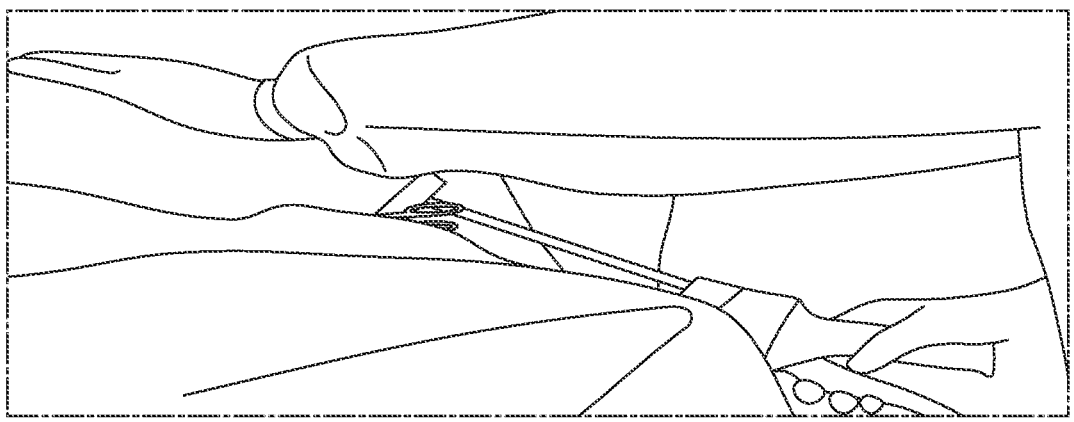
FIGS. 31A-31B show a surgical procedure for repairing a hernia defect.
Figure 31B:
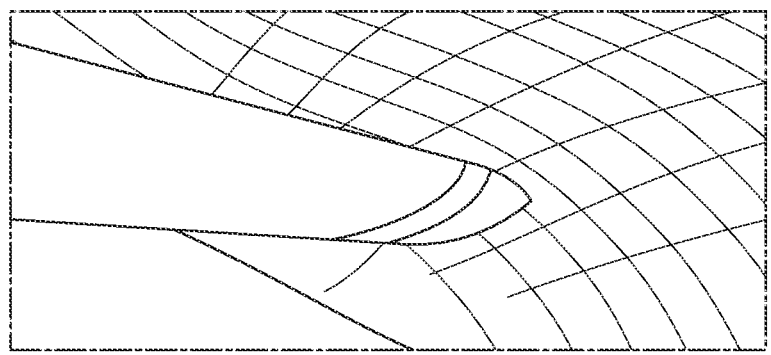

FIGS. 31A and 31B show a hernia repair procedure in which an applicator instrument having an elongated shaft passed through a trocar for accessing an abdominal cavity. As shown in FIG. 31B, in many instances it may be difficult for a surgeon to determine the orientation of the distal end of the elongated shaft relative to the mesh and the abdominal wall because the distal end cap is typically observed from below, behind, or to the sides of the distal end of the elongated shaft. If the dispensing window at the distal end of the elongated shaft is not properly oriented relative to the mesh, then the dispensed surgical fastener may not properly secure the mesh to the underlying abdominal wall. This is particularly true for applicator instruments in which the surgical fasteners are dispensed at an angle relative to the longitudinal axis of the elongated shaft. Thus, there is a need for distal end caps for applicator instruments that enable surgeons to quickly and easily determine the orientation of the distal end cap and the orientation of the dispensing window relative to the surgical mesh and the underlying tissue.

FIGS. 32A-43 show applicator instruments having end caps that provide visual indicia to a surgeon so that the surgeon may properly orient the instrument when dispensing surgical fasteners. Although the present invention is not limited by any particular theory of operation, it is believed that the visual indicia will allow a surgeon to quickly identify the location and the orientation of the dispensing window, as well as the orientation and location of the surgical fastener that will be dispensed from the dispensing window.

Figure 32A:
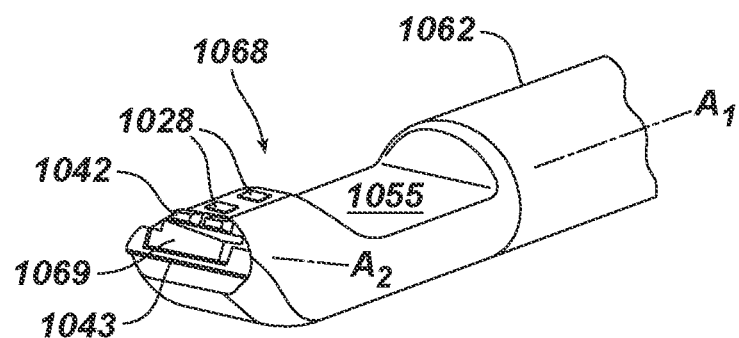
FIGS. 32A-32B show an application instrument having a distal end cap with visual indicia for orienting the applicator instrument during a surgical procedure.
Figure 32B:
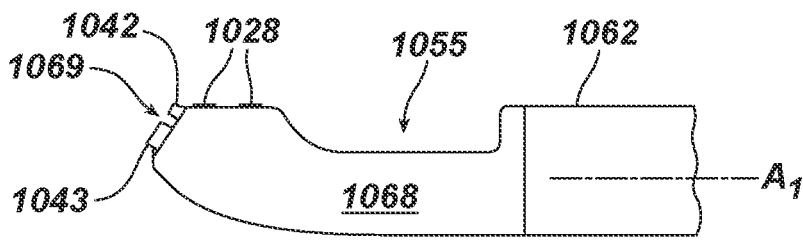

Referring to FIGS. 32A and 32B, in one embodiment, an applicator instrument 1050 includes an elongated shaft 1062 and a distal end cap 1068 secured to the distal end of the elongated shaft. The distal end cap 1068 has a surgical fastener dispensing window 1069 that is adapted to dispense a surgical fastener along an axis $A_2$ that defines an angle relative to the longitudinal axis $A_1$ of the elongated shaft 1062. The distal end cap has a first set of gripping elements 1028 that project from the top surface of the distal end cap 1068, and second and third gripping elements 1042, 1043 that bound the sides, top, and bottom of the dispensing window 1069. The distal end cap 1068 has a depression 1055 provided at the top surface that extends across the width of the end cap to enable a surgeon to determine the orientation of the dispensing window 1069.

Figure 33A:
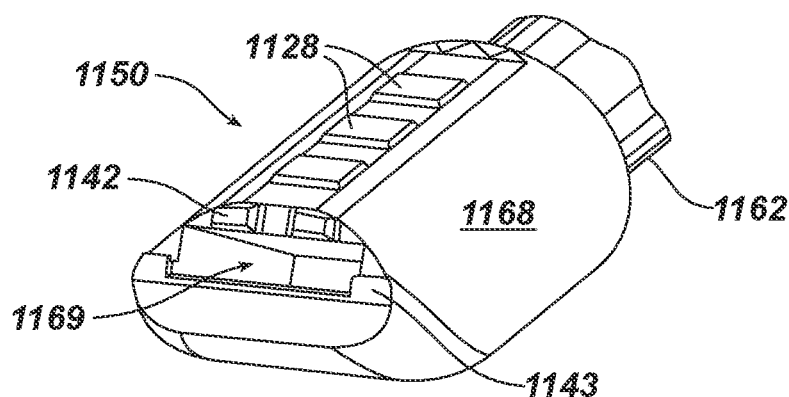
FIGS. 33A-33B show an application instrument having a distal end cap with visual indicia for orienting the applicator instrument during a surgical procedure.
Figure 33B:
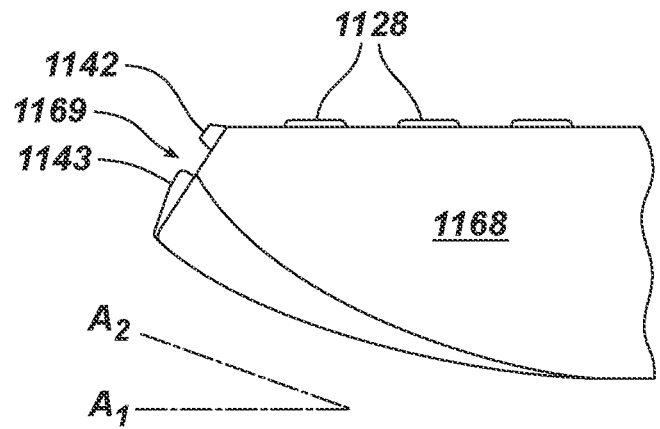

Referring to FIGS. 33A and 33B, in one embodiment, an applicator instrument 1150 includes an elongated shaft 1162 and a distal end cap 1168 secured to the distal end of the elongated shaft. The distal end cap 1168 has a surgical fastener dispensing window 1169 that is adapted to dispense a surgical fastener along an axis $A_2$ that defines an angle relative to the longitudinal axis $A_1$ of the elongated shaft 1162. The distal end cap has a first set of gripping elements 1128 that project from the top surface of the distal end cap 1168, and second and third gripping elements 1142, 1143 that bound the sides, top, and bottom of the dispensing window 1169. The distal end cap 1168 has a flat top surface and a curved bottom surface. The flat top surface, the curved bottom surface, and the gripping elements 1128, 1142 and 1143 may be used as visual guides to assist the surgeon in orienting the dispensing window 1169 relative to a mesh and an underlying abdominal wall.

Figure 34A:
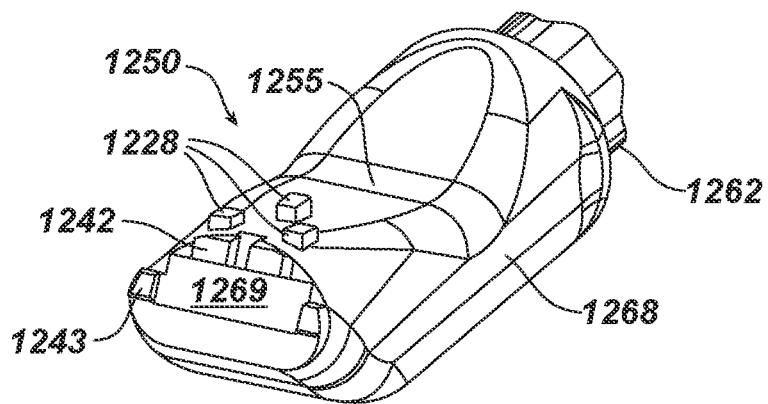
FIGS. 34A-34B show an application instrument having a distal end cap with visual indicia for orienting the applicator instrument during a surgical procedure.
Figure 34B:
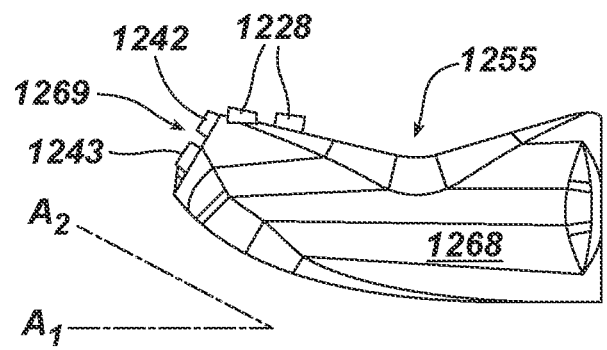

Referring to FIGS. 34A and 34B, in one embodiment, an applicator instrument 1250 includes an elongated shaft 1262 and a distal end cap 1268 secured to the distal end of the elongated shaft. The distal end cap 1268 has a surgical fastener dispensing window 1269 that is adapted to dispense a surgical fastener along an axis $A_2$ that defines an angle relative to the longitudinal axis $A_1$ of the elongated shaft 1262. The distal end cap has a first set of gripping elements 1228 that project from the top surface of the distal end cap 1268, and second and third gripping elements 1242, 1243 that bound the sides, top, and bottom of the dispensing window 1269. The distal end cap 1268 has a V-shaped depression 1255 provided at the top surface that extends across the width of the end cap. The distal end cap has a curved bottom surface. The V-shaped depression 1255, the curved bottom surface, and the gripping elements 1228, 1242 and 1243 may be used as visual guides to assist the surgeon in orienting the dispensing window 1269 relative to a mesh and an underlying abdominal wall.

Figure 35A:
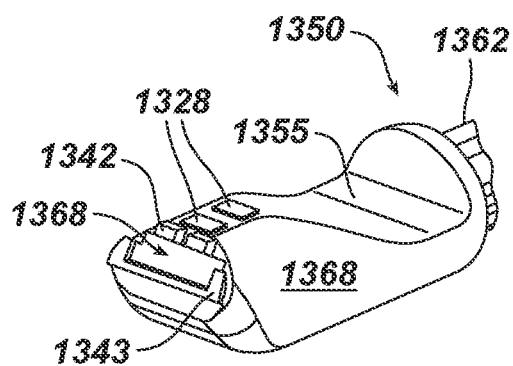
FIGS. 35A-35B show an application instrument having a distal end cap with visual indicia for orienting the applicator instrument during a surgical procedure.
Figure 35B:
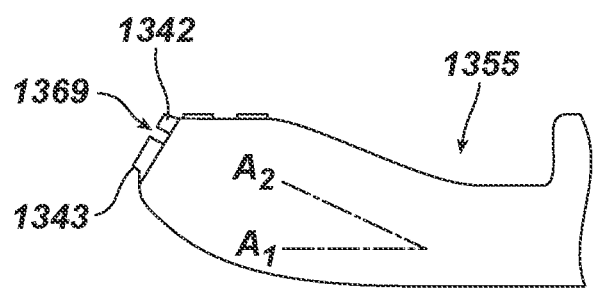

Referring to FIGS. 35A and 35B, in one embodiment, an applicator instrument 1350 includes an elongated shaft 1362 and a distal end cap 1368 secured to the distal end of the elongated shaft. The distal end cap 1368 has a surgical fastener dispensing window 1369 that is adapted to dispense a surgical fastener along an axis $A_2$ that defines an angle with the longitudinal axis $A_1$ of the elongated shaft 1362. The distal end cap has a first set of gripping elements 1328 that project from the top surface of the distal end cap 1368, and second and third gripping elements 1342, 1343 that bound the sides, top, and bottom of the dispensing window 1369. The distal end cap 1368 has a depression 1355 provided at the top surface that extends across the width of the end cap. The distal end cap has a curved bottom surface. The depression 1355, the curved bottom surface, and the gripping elements 1328, 1342 and 1343 may be used as visual guides to assist the surgeon in orienting the dispensing window 1369 relative to a mesh and an underlying abdominal wall.

Figure 36:
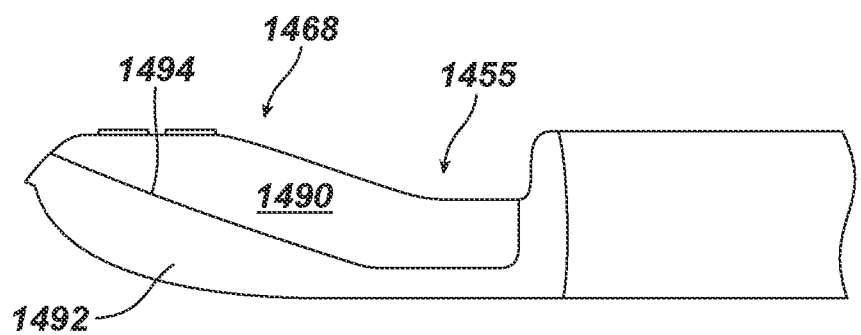
FIG. 36 shows an applicator instrument having a distal end cap with visual indicia for orienting the applicator instrument during a surgical procedure.

Referring to FIG. 36, in one embodiment, a distal end cap 1468 includes different colored sections to provide visual cues to the surgeon as to the orientation of the surgical fastener dispensing window and the axis upon which the surgical fastener will be dispensed from the dispensing window. In one embodiment, a top section 1490 of the end cap is made of a light color material and a bottom section 1492 of the end cap is made of a darker color material. In another embodiment, the distal end cap 1468 is one piece but printed with two colors. In one embodiment, the contrast between the top and bottom sections 1490, 1492 defines a boundary line 1494 extending between the top and bottom sections. The boundary line 1494 extends along an axis that intersects with the dispensing window and indicates the orientation and position of the surgical fastener as it is dispensed from the end cap. The distal end cap also has a depression 1455 that extends across the top and the width of the end cap that provides further visual cues for the surgeon. In one embodiment, the depression is replaced with a transparent component that provides the same effect without reducing the physical cross section of the distal end cap.

Figure 37:
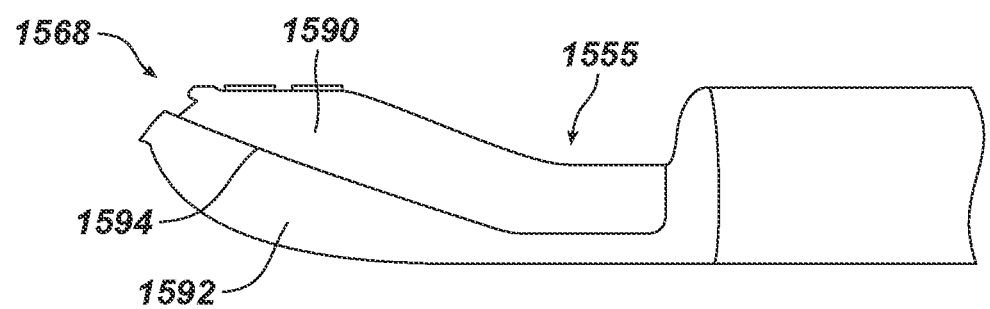
FIG. 37 shows an applicator instrument having a distal end cap with visual indicia for orienting the applicator instrument during a surgical procedure.

Referring to FIG. 37, in one embodiment, a distal end cap 1568 includes different colored sections to provide visual cues to the surgeon as to the orientation of the surgical fastener dispensing window and the axis upon which the surgical fastener will be dispensed from the dispensing window. In one embodiment, a top section 1590 of the end cap is made of a darker color material and a bottom section 1592 of the end cap is made of a lighter color material. In another embodiment, the distal end cap 1568 is one piece but printed with two colors. In one embodiment, the contrast between the top and bottom sections 1590, 1592 defines a boundary line 1594 extending between the top and bottom sections. The boundary line 1594 extends along an axis that intersects with the dispensing window and indicates the orientation of the surgical fastener as it is dispensed from the end cap. The distal end cap also has a depression 1555 that extends across the top and the width of the end cap that provides further visual cues for the surgeon. In one embodiment, the depression is replaced with a transparent component that provides the same effect without reducing the physical cross section of the distal end cap.

Figure 38:
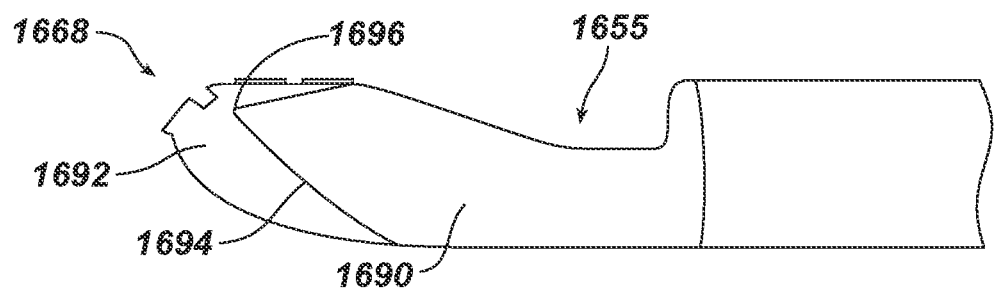
FIG. 38 shows an applicator instrument having a distal end cap with visual indicia for orienting the applicator instrument during a surgical procedure.

Referring to FIG. 38, in one embodiment, a distal end cap 1668 includes different colored sections to provide visual cues to the surgeon as to the orientation of the surgical fastener dispensing window and the axis upon which the surgical fastener will be dispensed from the dispensing window. In one embodiment, a proximal section 1690 of the end cap is made of a darker color material and a distal section 1692 of the end cap is made of a lighter color material. In one embodiment, the contrast between the distal and proximal sections 1690, 1692 defines an arrow shaped boundary line 1694 having a point 1696 that extends between the proximal and distal sections. The point 1696 of the arrow shaped boundary line 1694 is aligned with the dispensing window and indicates the orientation of the surgical fastener as it is dispensed from the end cap. The distal end cap also has a depression 1655 that extends across the top and the width of the end cap that provides further visual cues for the surgeon.

Figure 39:
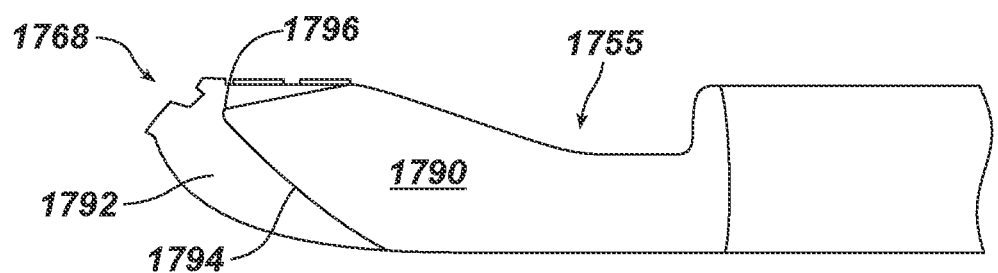
FIG. 39 shows an applicator instrument having a distal end cap with visual indicia for orienting the applicator instrument during a surgical procedure.

Referring to FIG. 39, in one embodiment, a distal end cap 1768 includes different colored sections to provide visual cues to the surgeon as to the orientation of the surgical fastener dispensing window and the axis upon which the surgical fastener will be dispensed from the dispensing window. In one embodiment, a proximal section 1790 of the end cap is made of a lighter color material and a distal section 1792 of the end cap is made of a darker color material. In one embodiment, the contrast between the distal and proximal sections 1790, 1792 defines an arrow shaped boundary line 1794 having a point 1796 that extends between the proximal and distal sections. The point 1796 of the arrow shaped boundary line 1794 is aligned with the dispensing window and indicates the orientation of the surgical fastener as it is dispensed from the end cap. The distal end cap also has a depression 1755 that extends across the top and the width of the end cap that provides further visual cues for the surgeon.

Figure 40:
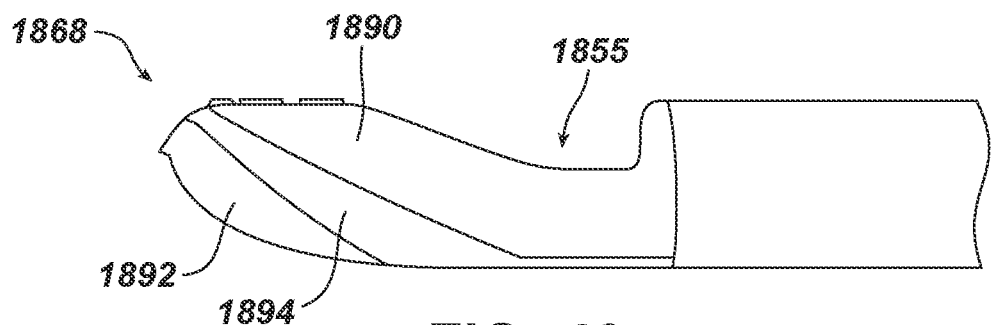
FIG. 40 shows an applicator instrument having a distal end cap with visual indicia for orienting the applicator instrument during a surgical procedure.

Referring to FIG. 40, in one embodiment, a distal end cap 1868 includes different colored sections to provide visual cues to the surgeon as to the orientation of the surgical fastener dispensing window and the axis upon which the surgical fastener will be dispensed from the dispensing window. In one embodiment, a top section 1890 of the end cap is made of a darker color material, a bottom section 1892 of the end cap is made of the same darker color material, and a band 1894 made of a light color material extends between the darker colored top and bottom sections 1890, 1892. The band 1894 extends from the bottom of the distal end cap to the sides of the distal end cap. The distal end of the lighter colored band 1894 is aligned with and intersects with the dispensing window, and indicates the orientation of the surgical fastener as it is dispensed from the distal end cap. The distal end cap also has a depression 1855 that extends laterally across the top and the width of the distal end cap that provides further visual cues for the surgeon.

Figure 41:
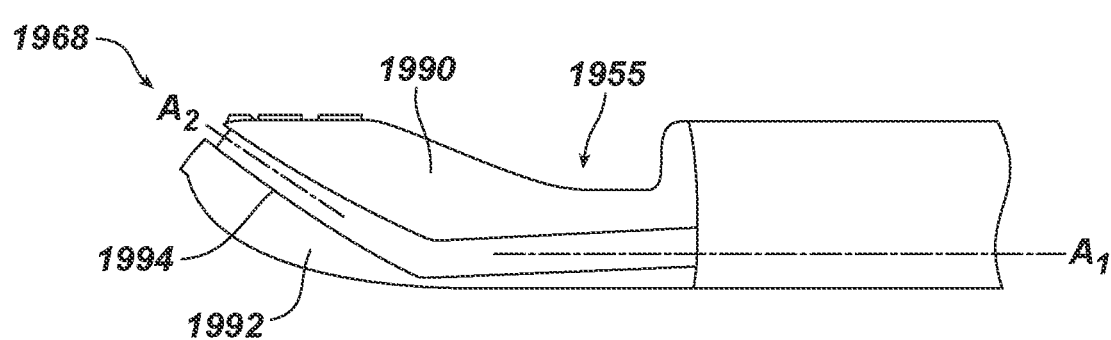
FIG. 41 shows an applicator instrument having a distal end cap with visual indicia for orienting the applicator instrument during a surgical procedure.

Referring to FIG. 41, in one embodiment, a distal end cap 1968 includes a top section 1990 made of a lighter color material, a bottom section 1992 that is also made of the lighter color material, and a band 1994 made of a darker color material that extends between the lighter colored top and bottom sections 1990, 1992. The band 1994 extends along the sides of the distal end cap. A proximal section of the darker colored band 1994 indicates the longitudinal axis $A_1$ of the elongated shaft and the distal section of the darker band is aligned with and intersects with the dispensing window. The distal section of the band indicates the orientation of the surgical fastener (i.e., aligned with axis $A_2$) as it is dispensed from the distal end cap. The distal end cap also has a depression 1955 that extends laterally across the top and the width of the distal end cap that provides further visual cues for the surgeon.

Figure 42:
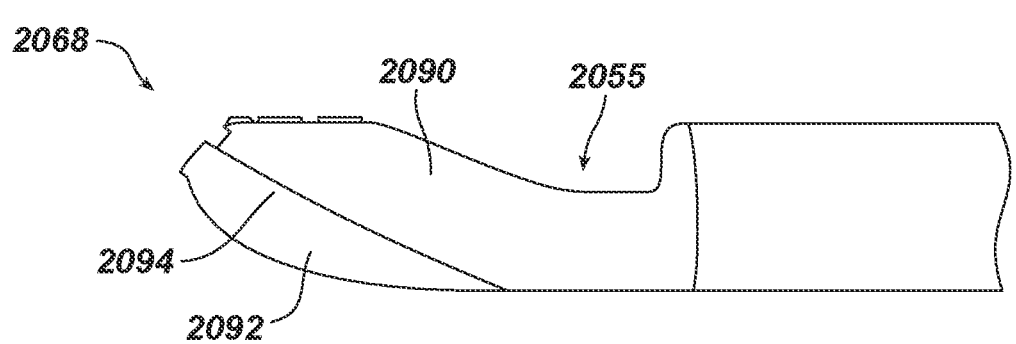
FIG. 42 shows an applicator instrument having a distal end cap with visual indicia for orienting the applicator instrument during a surgical procedure.

Referring to FIG. 42, in one embodiment, a distal end cap 2068 includes a top section 2090 made of a darker color material and a bottom section 2092 made of a lighter color material. In one embodiment, the contrast between the top and bottom sections 2090, 2092 defines a boundary line 2094 extending between the top and bottom sections. The boundary line 2094 extends from the bottom of the distal end cap to the sides of the distal end cap. The boundary line 2094 extends along an axis that intersects with the dispensing window and indicates the orientation of the surgical fastener as it is dispensed from the end cap. The distal end cap also has a depression 2055 that extends across the top and the width of the end cap that provides further visual cues for the surgeon.

Figure 43:
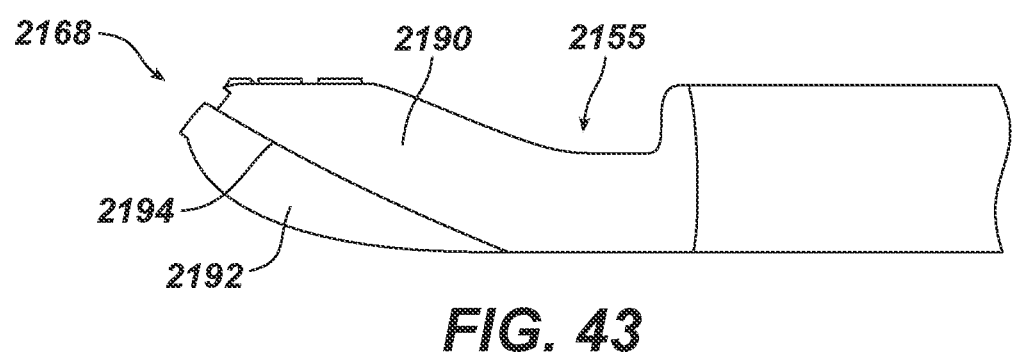
FIG. 43 shows an applicator instrument having a distal end cap with visual indicia for orienting the applicator instrument during a surgical procedure.

Referring to FIG. 43, in one embodiment, a distal end cap 2168 includes a top section 2190 made of a lighter color material and a bottom section 2192 made of a darker color material. In one embodiment, the contrast between the top and bottom sections 2190, 2192 defines a boundary line 2194 extending between the top and bottom sections. The boundary line 2194 extends from the bottom of the distal end cap to the sides of the distal end cap. The boundary line 2194 extends along an axis that intersects with the dispensing window and indicates the orientation of the surgical fastener as it is dispensed from the end cap. The distal end cap also has a depression 2155 that extends across the top and the width of the end cap that provides further visual cues for the surgeon.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An applicator nstrument for dispensing surgical fasteners comprising:
 a housing;
 an elongated shaft extending from said housing, said elongated shaft having a proximal end secured to said housing, a distal end spaced from the proximal end, and a first axis extending between the proximal and distal ends of said elongated shaft;
 a plurality of surgical fasteners disposed in said elongated shaft, wherein said surgical fasteners are stacked at an angle relative to the first axis of said elongated shaft;
 a distal end cap secured to the distal end of said elongated shaft, said distal end cap having a surgical fastener dispensing window;
 a firing system disposed in said housing, the firing system including a firing rod that extends through said elongated shaft to contact a distal-most one of the surgical fasteners so that distal movement of the firing rod dispenses the distal-most surgical fastener through the surgical fastener dispensing window, wherein said firing rod includes a proximal section with an extension that moves along the first axis, a distal section that moves along a second axis, and a joining member interconnecting said proximal section of said firing rod and said distal section of said firing rod, wherein said joining member has a proximal end that is pivotally coupled with a distal end of said proximal section of said firing rod and a distal end that is pivotally coupled with said distal section of said firing rod; and
 an actuator coupled with said firing system for activating said firing system to dispense said surgical fasteners distally through said surgical fastener dispensing window.

2. The applicator instrument as claimed in claim 1, wherein said surgical fasteners have respective lengths that extend along the second axis that defines the angle relative to the first axis of said elongated shaft, and wherein during a firing cycle said firing system advances a leading one of said surgical fasteners along the second axis for being dispensed through said surgical fastener dispensing window of said distal end cap.

3. The applicator instrument as claimed in claim 2, wherein the angle between the first axis of said elongated shaft and the second axis of said stacked surgical fasteners is about 30 degrees.

4. The applicator instrument as claimed in claim 3, wherein said distal end cap comprises an angled ramp configured to guide said surgical fasteners along the second axis toward said surgical fastener dispensing window.

5. The applicator instrument as claimed in claim 4, wherein said firing rod further comprises a pivoting member having an upper end with a first pivot point that is fixed inside said elongated shaft, a lower end with a second pivot point, and an elongated slot located between said first and second pivot points, wherein a distal end of said extension of said proximal section of said firing rod is pivotally secured to said pivoting member at said elongated slot, and wherein said second pivot point is pivotally connected with the proximal end of said joining member.

6. The applicator instrument as claimed in claim 5, wherein said elongated shaft includes an outer wall having an opening that is aligned with said second pivot point of said pivoting member, and wherein during a firing cycle the opening provides a space for enabling said pivoting member and said joining member to travel outside said outer wall of said elongated shaft.

7. The applicator instrument as claimed in claim 5, wherein said distal section of said firing rod comprises an insertion fork, and wherein the distal end of said joining member is pivotally connected with a proximal end of said insertion fork.

8. The applicator instrument as claimed in claim 7, wherein said surgical fasteners are configured for being loaded one at a time onto said insertion fork for being dispensed from said surgical fastener dispensing window along the second axis.

9. The applicator instrument as claimed in claim 7, wherein said insertion fork comprises opposing tines adapted to engage legs of said surgical fasteners, wherein said opposing tines are selected from the group consisting of tines having C-shaped cross-sections with openings that oppose one another, tines having proximal ends with C-shaped cross-sections having openings that oppose one another and distal ends having L-shaped cross-sections having openings that oppose one another, and tines having lengths with L-shaped cross-sections having openings that oppose one another.

10. The applicator instrument as claimed in claim 9, wherein said opposing tines are moveable between an open position in which said opposing tines are further apart and a closed position in which said opposing tines are closer together, wherein said insertion fork includes a spring providing a force that normally urges said opposing tines into the open position, and wherein said applicator instrument includes a cam surface that engages said insertion fork during a firing cycle for overcoming the force of said spring and urging said opposing tines into the closed position.

11. The applicator instrument as claimed in claim 5, wherein during an initial stage of a firing cycle said proximal section of said firing rod extends along the first axis, said joining member extends along a third axis that is parallel with the first axis, and said distal section of said firing rod extends along the second axis, and wherein during a later stage of said firing cycle said proximal section of said firing rod extends along the first axis, and said joining member and said distal section of said firing rod extend along the second axis.

12. The applicator instrument as claimed in claim 7, wherein said angled ramp guides movement of said distal section of said firing rod along the second axis when dispensing said surgical fasteners from said surgical fastener dispensing window of said distal end cap.

13. The applicator instrument as claimed in claim 12, wherein said distal end cap has a top surface and a distal end face that extends within a plane that is perpendicular to the second axis, and wherein said top surface of said distal end cap has a first set of spaced protrusions and said distal end face has a second set of spaced protrusions.

14. The applicator instrument as claimed in claim 12, wherein said distal end cap has a top cap part and a bottom cap part that are assembled together, wherein said top cap part defines a ceiling of said angled ramp and said bottom cap part defines a floor of said angled ramp, and wherein said surgical fastener dispensing window is located at a distal-most end of said angled ramp and is bounded by said ceiling of said top cap part and said floor of said bottom cap part.

15. The applicator instrument as claimed in claim 1, wherein said distal end cap has a first section having a first color and a second section having a second color that contrasts with the first color to define a color contrasting boundary that provides visual indicators of an orientation of said distal end cap and a location of said surgical fastener dispensing window.

16. An applicator instrument for dispensing surgical fasteners comprising:
a housing;
an elongated shaft extending from said housing, said elongated shaft including a proximal end secured to said housing, a distal end spaced from the proximal end, and a first axis extending between the proximal and distal ends;
a plurality of stacked surgical fasteners disposed in said elongated shaft;
a distal end cap secured to the distal end of said elongated shaft, said distal end cap having a surgical fastener dispensing window and a ramp configured for guiding said surgical fasteners toward said surgical fastener dispensing window, wherein said ramp extends along a second axis that defines an angle relative to the first axis of said elongated shaft;
a firing system disposed in said housing, the firing system including a firing rod that extends through said elongated shaft to contact a distal-most one of the surgical fasteners so that distal movement of the firing rod dispenses the distal-most surgical fastener through the surgical fastener dispensing window, wherein said firing rod includes a proximal section with an extension that moves along the first axis, a distal section that moves along the second axis, and a joining member interconnecting said proximal section of said firing rod and said distal section of said firing rod, wherein said joining member has a proximal end that is pivotally coupled with a distal end of said proximal section of said firing rod and a distal end that is pivotally coupled with said distal section of said firing rod; and
an actuator coupled with said housing to move the firing rod distally to advance distal-most surgical fastener over said ramp extending along the second axis for dispensing the distal-most surgical fastener distally from said surgical fastener dispensing window of said distal end cap.

17. The applicator instrument as claimed in claim 16, wherein said stacked surgical fasteners have respective lengths that are parallel with the second axis of said ramp that defines the angle relative to the first axis of said elongated shaft.

18. The applicator instrument as claimed in claim 17, wherein the angle defined by the first axis and the second axis of said ramp is about 30 degrees.

19. A method of dispensing surgical fasteners comprising:
providing an applicator instrument including an elongated shaft having a proximal end, a distal end, and a longitudinal axis extending between the proximal and distal ends of said elongated shaft;
disposing a plurality of surgical fasteners inside said elongated shaft with said surgical fasteners stacked at an angle relative to the longitudinal axis of said elongated shaft; and
moving distally a firing rod including a proximal section with an extension that moves along the first axis, a distal section that moves along the second axis, and a joining member having a proximal end pivotally connected to the distal end of the proximal section and a distal end pivotally coupled to the distal section to dispense said surgical fasteners distally from the distal end of said elongated shaft with said surgical fasteners oriented at the angle relative to the longitudinal axis of said elongated shaft.

\* \* \* \* \*

UNITED STATES PATENT AND TRADEMARK OFFICE
CERTIFICATE OF CORRECTION

| | |
|---|---|
| PATENT NO. | : 11,491,000 B2 |
| APPLICATION NO. | : 16/421805 |
| DATED | : November 8, 2022 |
| INVENTOR(S) | : Cardinale et al. |

It is certified that error appears in the above-identified patent and that said Letters Patent is hereby corrected as shown below:

In the Claims

Claim 1, Column 27, Line 2:
"An applicator nstrument for dispensing surgical fasten-" should read "An applicator instrument for dispensing surgical fasten-".

Claim 16, Column 29, Line 34:
"rod distally to advance distal-most surgical fastener" should read "rod distally to advance the distal-most surgical fastener".

Signed and Sealed this
Thirteenth Day of December, 2022

*Katherine Kelly Vidal*
Katherine Kelly Vidal
*Director of the United States Patent and Trademark Office*